US012275933B2

(12) United States Patent
Karande et al.

(10) Patent No.: US 12,275,933 B2
(45) Date of Patent: Apr. 15, 2025

(54) COMPOSITION OF PHOTOAUTOTROPHIC MICROORGANISMS AND CHEMOHETEROTROPHIC MICROORGANISMS IN A BIOFILM

(71) Applicant: Helmholtz-Zentrum für Umweltforschung GmbH—UFZ, Leipzig (DE)

(72) Inventors: Rohan Karande, Leipzig (DE); Ingeborg Heuschkel, Leipzig (DE); Katja Bühler, Leipzig (DE); Anna Hoschek, Leipzig (DE); Andreas Schmid, Leipzig (DE)

(73) Assignee: Helmholtz-Zentrum für Umweltforschung GmbH—UFZ, Leipzig (DE)

( * ) Notice: Subject to any disclaimer, the term of this patent is extended or adjusted under 35 U.S.C. 154(b) by 634 days.

(21) Appl. No.: 17/276,075

(22) PCT Filed: Sep. 13, 2018

(86) PCT No.: PCT/EP2018/074746
§ 371 (c)(1),
(2) Date: Mar. 12, 2021

(87) PCT Pub. No.: WO2020/052762
PCT Pub. Date: Mar. 19, 2020

(65) Prior Publication Data
US 2022/0049210 A1    Feb. 17, 2022

(51) Int. Cl.
*C12N 1/20* (2006.01)
*C12M 1/00* (2006.01)
*C12M 1/12* (2006.01)
*C12P 7/22* (2006.01)
*C12P 17/08* (2006.01)
*C12P 39/00* (2006.01)

(52) U.S. Cl.
CPC .............. *C12N 1/20* (2013.01); *C12M 21/02* (2013.01); *C12M 23/06* (2013.01); *C12M 23/22* (2013.01); *C12M 25/06* (2013.01); *C12P 7/22* (2013.01); *C12P 17/08* (2013.01); *C12P 39/00* (2013.01)

(58) Field of Classification Search
CPC ......... C12N 1/20; C12M 21/02; C12M 23/06; C12M 23/22; C12M 25/06; C12M 25/00; C12P 7/22; C12P 17/08; C12P 39/00; C12P 7/02
See application file for complete search history.

(56) References Cited

FOREIGN PATENT DOCUMENTS

WO    2018046104 A1    3/2018

OTHER PUBLICATIONS

Koenig, A., Zhang, T., Liu, L. H., & Fang, H. H. (2005). Microbial community and biochemistry process in autosulfurotrophic denitrifying biofilm. Chemosphere, 58(8), 1041-1047. (Year: 2005).*
Gallucci, K. K., & Paerl, H. W. (1983). Pseudomonas aeruginosa chemotaxis associated with blooms of N2-fixing blue-green algae (*cyanobacteria*). Applied and Environmental Microbiology, 45(2), 557-562. (Year: 1983).*
Karande, et al. (2016). Continuous cyclohexane oxidation to cyclohexanol using a novel cytochrome P450 monooxygenase from *Acidovorax* sp. CHX100 in recombinant *P. taiwanensis* VLB120 biofilms. Biotechnology and bioengineering, 113(1), 52- (Year: 2016).*
Abed, R. M. (2010). Interaction between cyanobacteria and aerobic heterotrophic bacteria in the degradation of hydrocarbons. International Biodeterioration & Biodegradation, 64(1), 58-64. (Year: 2010).*
Mallick, I., Kirtania, P., Szabó, M., Bashir, F., Domonkos, I., Kos, P. B., & Vass, I. (2020). A simple method to produce Synechocystis PCC6803 biofilm under laboratory conditions for electron microscopic and functional studies. Plos one, 15(7), e0236842. (Year: 2020).*
Hoschek, A., Bühler, B., & Schmid, A. (2017). Overcoming the gas-liquid mass transfer of oxygen by coupling photosynthetic water oxidation with biocatalytic oxyfunctionalization. Angewandte Chemie International Edition, 56(47), 15146-15149. (Year: 2017).*
Villa, F., Pitts, B., Lauchnor, E., Cappitelli, F., & Stewart, P. S. (2015). Development of a laboratory model of a phototroph-heterotroph mixed-species biofilm at the stone/air interface. Frontiers in Microbiology, 6, 1251. (Year: 2015).*
Bakalar, N. (May 23, 2016). Earth May Be Home to a Trillion Species of Microbes. The New York Times. https://www.nytimes.com/2016/05/24/science/one-trillion-microbes-on-earth.html#:~:text=According%20to%20a%20new%20estimate (Year: 2016).*
Microbiology. (May 8, 2017). Biology Libre Texts. https://bio.libretexts.org/Bookshelves/Microbiology/Microbiology_(Boundless)/05%3A_Microbial_Metabolism/5.01%3A_Types_of_Metabolism/5.1B%3A_Chemoautotrophs_and_Chemohetrotrophs (Year: 2017).*
Löwe, H., Hobmeier, K., Moos, M., Kremling, A., & Pflüger-Grau, K. (2017). Photoautotrophic production of polyhydroxyalkanoates in a synthetic mixed culture of Synechococcus elongatus cscB and Pseudomonas putida cscAB. Biotechnology for biofuels, 10, 1-11. (Year: 2017).*
Yannarell SMGrandchamp GMChen S, Daniels KE, Shank EA 2019. A Dual-Species Biofilm with Emergent Mechanical and Protective Properties. J Bacteriol 201:10.1128/jb.00670-18. https://doi.org/10.1128/jb.00670-18 (Year: 2019).*

(Continued)

*Primary Examiner* — Louise W Humphrey
(74) *Attorney, Agent, or Firm* — ArentFox Schiff LLP

(57) ABSTRACT

A composition of microorganisms, comprising
 photoautotrophic microorganisms (16) which produce oxygen by photosynthetic water oxidation
 chemoheterotrophic microorganisms (17) which respire oxygen, wherein the photoautotrophic microorganisms (16) and the chemoheterotrophic microorganisms (17) are comprised in a biofilm (13), the biofilm further comprising components (15) which were secreted by the photoautotrophic microorganisms (16) and/or the chemoheterotrophic microorganisms (17),
and a reactor (1), a method for forming a biofilm, and a method for biocatalytic conversion employing such composition.

14 Claims, 4 Drawing Sheets

Specification includes a Sequence Listing.

(56) References Cited

OTHER PUBLICATIONS

Kalíková, G., & Bundschuh, M. (2022). Aquatic biofilms—sink or source of microplastics? A critical reflection on current knowledge Environmental Toxicology and Chemistry, 41(4), 838-843. (Year: 2022).*

Herrera-Belaroussi, A., Cockell, C. S., Self, S., Blaxter, M., Reitner, J., Arp, G., . . . & Tindle, A. G. (2008). Bacterial colonization and weathering of terrestrial obsidian in Iceland. Geomicrobiology Journal, 25(1), 25-37. (Year: 2008).*

Gerdes, G. (2007). Structures left by modern microbial mats in their host sediments. In Atlas of microbial mat features preserved within the siliciclastic rock record (p. 5). (Year: 2007).*

Li, Z., Quan, G., Jiang, X., Yang, Y., Ding, X., Zhang, D., . . . & Zhu, G. (2018). Effects of metabolites derived from gut microbiota and hosts on pathogens. Frontiers in cellular and infection microbiology, 8, 392647. (Year: 2018).*

Wishart DS, Tzur D, Knox C, et al., HMDB: the Human Metabolome Database. Nucleic Acids Res. Jan. 2007;35(Database issue): D521-6. 17202168 retrieved on Mar. 27, 2024 from https://hmdb.ca/metabolites/HMDB0031264 (Year: 2024).*

David, Christian, et al., "Stabilization of single species Synechocystis biofilms by cultivation under segmented flow, Journal of Industrial Microbiology and Biotechnology", vol. 42, No. 7, May 2015, pp. 1083-1089.

Cole, Jessica K., et al., "Phototrophic biofilm assembly in microbial-mat-derived unicyanobacterial consortia: model systems for the study of autotroph-heterotroph interactions", Frontiers in Microbiology, vol. 5, Apr. 7, 2014, 26 pages.

Adlercreutz, P., et al., "Oxygen supply to immobilized cells: 2. Studies on a coimmobilized algae-bacteria preparation with in situ oxygen generation", Enzyme and Microbial Technology, vol. 4, No. 6, Nov. 1, 1982.

Hoschek, Anna, et al., "Overcoming the Gas-Liquid Mass Transfer of Oxygen by Coupling Photosynthetic Water Oxidation with Biocatalytic Oxyfunctionalization", Angewandte Chemie International Edition, vol. 56, No. 47, Nov. 20, 2017, 13 pages.

International Search Report and Written Opinion for PCT/EP2018/074746, dated Mar. 25, 2019, 14 pages.

M. G. Panke, S; Witholt, B; Schmid, A; Wubbolts, "Towards a biocatalyst for (S)-styrene oxide production: characterization of the styrene degradation pathway of *Pseudomonas* sp. strain VLB120," Appl Env Microbiol 1998; 64:2032-2043.

R. Y. Stanier, R. Kunisawa, M. Mandel, and G. Cohen-Bazire, "Purification and properties of unicellular blue-green algae (Order Chroococcales).," Bacteriol Rev 1971; 35:171-205.

A. David, C.; Bühler, K.; Schmid, "Stabilization of single species *Synechocysitis* biofilms by cultivation under segmented flow," J Ind Microbiol Biotechnol 2015; 42:1083-1089.

Emmerling, M., et al., Metabolic flux responses to pyruvate kinase knockout in *Escherichia coli*. J Bacteriol 2002; 184:152-164.

* cited by examiner

A

B

C

SEQUENCE LISTING

```
<160> NUMBER OF SEQ ID NOS: 6

<210> SEQ ID NO 1
<211> LENGTH: 69
<212> TYPE: DNA
<213> ORGANISM: Artificial Sequence
<220> FEATURE:
<223> OTHER INFORMATION: primer sequence

<400> SEQUENCE: 1
tgagcggata acaatttcac acatactaga gtagtggagg ttactagatg aaaaaaaccc    60
aacatctgg                                                             69

<210> SEQ ID NO 2
<211> LENGTH: 77
<212> TYPE: DNA
<213> ORGANISM: Artificial sequence
<220> FEATURE:
<223> OTHER INFORMATION: premier sequence

<400> SEQUENCE: 2
tcgttttatt tgatgcctgg ctgcactatt tttcgaactg cgggtggctc caagcgctct    60
ggaatacgaa accctcg                                                    77

<210> SEQ ID NO 3
<211> LENGTH: 67
<212> TYPE: DNA
<213> ORGANISM: artificial sequence
<220> FEATURE:
<223> OTHER INFORMATION: primer sequence

<400> SEQUENCE: 3
tgagcggata acaatttcac acatactaga gtagtggagg ttactagatg actcagactg    60
ctgcggc                                                               67
```

```
<210> SEQ ID NO 4
<211> LENGTH: 42
<212> TYPE: DNA
<213> ORGANISM: Artificial sequence
<220> FEATURE:
<223> OTHER INFORMATION: primer sequence

<400> SEQUENCE: 4
ctttcgtttt atttgatgcc tggtatcagt gctgcccttg cg                    42

<210> SEQ ID NO 5
<211> LENGTH: 50
<212> TYPE: DNA
<213> ORGANISM: artificial sequence
<220> FEATURE:
<223> OTHER INFORMATION: primer sequence

<400> SEQUENCE: 5
gggaggtatt ggaccgcatt gaactctagt atataaacgc agaaaggccc            50

<210> SEQ ID NO 6
<211> LENGTH: 50
<212> TYPE: DNA
<213> ORGANISM: artificial sequence
<220> FEATURE:
<223> OTHER INFORMATION: primer sequence

<400> SEQUENCE: 6
acgagccgga tgattaattg tcaatctaga gccaggcatc aaataaaacg            50
```

COMPOSITION OF PHOTOAUTOTROPHIC MICROORGANISMS AND CHEMOHETEROTROPHIC MICROORGANISMS IN A BIOFILM

CROSS-REFERENCE TO RELATED APPLICATIONS

This application is a National Stage of PCT/EP2018/074746, filed on Sep. 13, 2018, the disclosure of which is incorporated herein by reference in its entirety.

FIELD OF THE INVENTION

The present invention relates to a composition of photoautotrophic microorganisms and chemoheterotrophic microorganisms in a biofilm, a reactor, and a method employing such composition.

BACKGROUND OF THE INVENTION

Utilizing microorganisms for biocatalytic purposes is a promising approach for the eco-efficient production of chemicals.

Alongside the development of catalytically efficient strains, the need for economically valuable reactor technology still challenges the bioprocess design. Catalyst-coated capillary reactors show great promise for the establishment of efficient continuous bioprocesses, due to an exceptionally high surface area to volume ratio (2000-4000 $m^2m^{-3}$ Karande, R. et al. *Biotechnol. Bioeng.* 111, 1831-1840 (2014)). Applying the microbial catalyst in a biofilm format further intensifies this technology, featuring self-immobilization, regeneration and high biomass retention (Rosche, B., et al. *Trends Biotechnol.* 27, 636-643 (2009); Halan, B. et al., *Trends Biotechnol.* 30, 453-465 (2012)).

The application of capillary reactors for biofilm cultivation shows great promise for the development of continuous bioprocesses. However, depending on the strain cultivated, such systems suffer from $O_2$ limitation or oversupply. Two main issues restrict the application of microorganisms in capillary reactors:
  i) not all biocatalytic relevant microorganisms form (stable) biofilms
  ii) as a consequence of $O_2$ respiration or $O_2$ evolution, dense cultivation of microbes results in a microenvironment either being $O_2$ limited or $O_2$ supersaturated, respectively (Karande, R. et al., *Biotechnol. Bioeng.* 111, 1831-1840 (2014); Huang et al., *Engineering* 3, 318-329 (2017)).

Much research is conducted on understanding and engineering biofilm formation, e.g., by altering genetic circuits and cell signaling (Wood, T. K. et al., *Trends Biotechnol.* 29, 87-94 (2011)). In addition, technical approaches, such as the supply of air segments into capillary reactors (Karande, R. et al., *Biotechnol. Bioeng.* 111, 1831-1840 (2014)) or by the application of membrane microreactors, aim at increasing the oxygen supply and mass transfer between aqueous and gas phase. (Gross, R. et al., *Biotechnol. Bioeng.* 98, 1123-1134 (2007)).

In nature, oxygenic phototrophs and aerobic heterotrophs are embedded in a complex matrix of extracellular polymeric substances (EPS) to form stable microbial mats (Prieto-Barajas, C. M. et al., *Electron. J. Biotechnol.* (2017)). The consortium interacts in a symbiotic relationship by exploiting complementary metabolic activities, inter alia, controlled by the exchange of $O_2$. Already some decades ago the phenomenon of in situ $O_2$ supply was transferred to biotechnology utilizing defined co-cultures of algae and bacteria (Adlercreutz, P. et al., *Enzyme Microb. Technol.* 4, 332-336 (1982); Adlercreutz, P. et al., *Enzyme Microb. Technol.* 4, 395-400 (1982)). Several further studies exemplified this idea (O'Reilly et al., *Enzyme Microb. Technol.* 17, 636-646 (1995)), e.g., for the lipid production by co-cultivating microalgae and yeast (Cheirsilp, B. et al., *New Biotechnol.* 28, 362-368 (2011); Papone, T. et al., *World Acad. Sci. Eng. Technol.* 64, 1127-1131 (2012)). Yet, this research focused on immobilized cells embedded in artificial polymers such as alginate, or cell suspensions.

Photoautotrophic organisms exploit cheap inorganic carbon ($CO_2$), water, and light energy for growth and are considered to be future cell factories for the production of fuels and chemicals from carbon dioxide. However, applications of phototrophic organisms in photobioreactors (PBR) for developing industrial scale processes are still considered to be challenging. An efficient PBR design should be economically viable and should couple light, hydrodynamics, mass transfer, cell growth and retention for maximizing process performance. Phototrophic cultures are currently practiced in different PBRs such as tubular, column airlift and flat-panel airlift reactors but low biomass within these reactor formats limits its commercial exploitation.

Application of microbial catalyst in biofilms benefits from its unique features such as self-immobilization, regeneration, and retention of high biomass within the reactor. The application of biofilms in a segmented flow capillary reactor as well as a method to convert a substrate to a value added product using biofilm as catalyst in above mentioned reactor have been previously described in the patent application WO 2012/152337.

OBJECTIVE OF THE INVENTION

The objective of the invention was to provide with a composition allowing improved biofilm formation, for example to allow the composition to be employed in bioreactors.

A further object of the present invention was to provide a method adapted to the cultivation of photoautotrophic organisms.

SUMMARY OF THE INVENTION

The invention provides a composition of microorganisms, a reactor, and a method according to the independent claims. Further embodiments of the invention are laid down in the dependent claims and in the following description and examples.

The invention provides a composition of microorganisms, comprising
  photoautotrophic microorganisms which produce oxygen by photosynthetic water oxidation
  chemoheterotrophic microorganisms which respire oxygen,
wherein the photoautotrophic microorganisms and the chemoheterotrophic microorganisms are comprised in a biofilm, the biofilm further comprising components which were secreted by the photoautotrophic microorganisms and/or the chemoheterotrophic microorganisms.

Said composition may also be called a composition of microorganisms in a biofilm, a biofilm, or a biofilm comprising said organisms.

In a further aspect, the invention provides a method for producing such composition, the method comprising cultivating a mixture of photoautotrophic microorganisms and chemoheterotrophic microorganisms, particularly on a surface.

In a further aspect, the invention provides a reactor, particularly a capillary reactor, comprising the composition of one of the invention wherein the biofilm extends along a surface, preferably along an inner surface of the reactor.

In still a further aspect, the invention provides a method reacting a substrate, preferably an organic substrate, to a product, comprising providing a reactor of the invention, the reactor comprising a composition of the invention,
contacting the composition with the substrate,
exposing the composition to light,
reacting the substrate to obtain the product.

The present invention provides, in the basic concept, or in one or more specific embodiments with one or more concepts or advantages mentioned below and in the further description.

It has been shown that improved biofilm formation can be reached, particularly improved amount or mass or volume of biofilm. Moreover, high cell density of photoautotrophic microorganisms and/or chemoheterotrophic microorganisms can be reached.

The results of the invention suggest a synergistic action of photoautotrophic microorganisms and chemoheterotrophic microorganisms in forming a biofilm. Particularly, a synergistically higher mass of biofilm may be reached when cultivating both organisms together.

In particular, the present invention comprises a defined consortium of photoautotrophic and chemoheterotrophic microorganisms, particularly bacteria, with complementary metabolic activities in a biofilm to reach and maintain a high cell-density (for example 30-48 $g_{CDW}$/L). This consortium can particularly be used for performing a biotransformation reaction or fermentation. Such biofilm can be used in a reactor and a method of the invention.

Increased biofilm formation is technically useful, for example for producing higher mass of the photoautotrophic organism. Biofilm, particularly with high amount of photoautotrophic organism, can for example be used in bioremediation, gas purification, and waste water treatment, such as for extraction of metabolites or cleaning pollutants from air or water.

In a more special aspect, biofilm is used for carrying out a reaction of interest when one or more of the organisms comprised in the biofilm are capable to convert a substrate to a product of interest, which is also called a value added product. Particularly, the photoautotrophic microorganisms and/or chemoheterotrophic microorganisms can be, or may be genetically modified in a way so that they are capable to catalyze, or carry out, such reaction. Reactions of interest are for example oxidation reactions of organic substrates in order to obtain valuable products.

The here presented method provides a defined and minimized (in terms of the reactor environment) biofilm system which is suitable for carrying out processes of interest, for example producing value added products. In the invention it is possible to convert an extracellular added substrate into a value added product.

In the method of the invention, the composition of the invention, particularly the photoautotrophic microorganisms and/or the chemoheterotrophic microorganisms and/or extracellular enzymes in the polymeric substances may act as catalyst. The photoautotrophic microorganisms and/or the chemoheterotrophic microorganisms may possess catalytic activity to transform an extracellular added substrate to a product. The catalytic activity may be introduced or may be based on genetic modification.

In this sense, the current invention concerns photobioreactors, specifically segmented flow photo-capillary for cultivation of bacterial biofilms, and processes utilizing biofilms as biocatalyst to produce valued added products or compounds.

The present invention provides with an improved method to harmonize (microbial) oxygen demand and supply for the robust cultivation of bacterial biofilms, particularly in a multiphase capillary reactor.

In the invention, two microbial species with complementary metabolic activities are employed, particularly in a capillary reactor, featuring proto-cooperation with enhanced biomass retention. By choosing strains from different trophies the issue of $O_2$ limitation or supersaturation is relieved. A chemoheterotrophic organism (for example *Pseudomonas* sp. VLB120) respires $O_2$, while a photoautotrophic organism (for example *Synechocystis* sp. PCC 6803) evolves $O_2$ by photosynthetic water oxidation, resulting in an $O_2$-optimized microenvironment. Depending on the intended application, the biofilm composition can be regulated by the addition of an organic carbon source.

The invention provides a method based on proto-cooperation mainly relying on $O_2$ exchange for co-cultivation of two microbial species from different trophies enabling robust and simple biofilm capillary reactor operation.

The present invention relates to a method to balance the supply and demand of $O_2$ within this consortium by choosing a photoautotrophic strain (*Synechocystis* sp. PCC 6803) that generates $O_2$ by photosynthetic water oxidation, and a chemoheterotrophic strain that respires $O_2$. In addition, the present invention concerns a method to extract $O_2$ produced by the photosynthetic water oxidation using oxygenase based enzymes within the chemoheterotrophic and/or the photoautotrophic organism to produce value added products or compounds.

In a further aspect of the cooperation of the microorganisms, the photoautotrophic organism may utilize carbon dioxide which is produced by the chemoheterotrophic organism when metabolizing an organic compound, as a substrate, and use such carbon dioxide to create biomass. In addition, the chemoheterotrophic organism may utilize organic compounds produced by the photoautotrophic organism when metabolizing an inorganic compound, and use such organic compounds to create biomass.

DETAILED DESCRIPTION OF THE INVENTION

Before the invention is described in detail with respect to some of its preferred embodiments, the following general definitions are provided.

The present invention as illustratively described in the following may suitably be practiced in the absence of any element or elements, limitation or limitations, not specifically disclosed herein.

Where the term "comprising" is used in the present description and claims, it does not exclude other elements. For the purposes of the present invention, the term "consisting of" is considered to be a preferred embodiment of the term "comprising of". If hereinafter a group is defined to comprise at least a certain number of embodiments, this is also to be understood to disclose a group which preferably consists only of these embodiments.

Where an indefinite or definite article is used when referring to a singular noun, e.g. "a", "an" or "the", this includes a plural of that noun unless something else is specifically stated. The terms "about" or "approximately" in the context of the present invention denotes an interval of accuracy that the person skilled in the art will understand to still ensure the technical effect of the feature in question. The term typically indicates deviation from the indicated numerical value of ±10%, and preferably of ±5%.

Photoautotrophic microorganisms are capable to produce organic compounds (such as carbohydrates, fats, and proteins) from simple, usually inorganic, compounds, thereby using light as energy source. For example, photoautotrophic microorganisms can exploit water as an electron source, use light as an energy source, and fix $CO_2$ as a carbon source. Photoautotrophic microorganisms are a special case of phototrophic microorganisms.

Production of oxygen by photosynthetic water oxidation means particularly the following reaction, carried out by the photoautotrophic microorganisms:

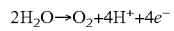

$$2H_2O \rightarrow O_2 + 4H^+ + 4e^-$$

Chemoheterotrophic microorganisms use organic compounds that are already available, and not self-produced by the chemoheterotrophic microorganism, as energy source. Chemoheterotrophic organisms are unable to fix carbon to form their own organic compounds. So, chemoheterotrophic microorganisms use organic compounds both as energy source and as carbon source.

In an embodiment of the invention, the photoautotrophic microorganisms and/or the chemoheterotrophic microorganisms are capable of catalyzing the conversion of a substrate, which is preferably an organic compound, into a product. The photoautotrophic microorganisms and/or the chemoheterotrophic microorganisms here act as a catalyst, specifically biocatalyst.

A substrate in the present invention may be a substrate or may be a compound that is naturally metabolized by the organism, particularly by the wild type organism. It is possible to gain a valuable product or intermediate product from such substrate or compound. Such substrate is also called "natural substrate". The natural substrate may be an organic compound, or an organic carbon source.

A substrate in the in the present invention, may, as alternative, be a substrate that is not naturally metabolized by the organism, particularly not metabolized by the wild type organism. Such substrate is also called "non-natural substrate". The non-natural substrate may be an organic compound.

A substrate may also be called "an educt".

The conversion may be an oxidation reaction. In the invention, oxygen that is produced by the photoautotrophic microorganisms may be predominantly or solely used for such oxidation. Further oxygen may be supplied, for example oxygen from air. Oxygen supply may be done by a reactor using segmented flow, as described in this description at other place.

As indicated above, the substrate may be a substrate that is naturally metabolized by the organism (particularly the wild type organism), for example glucose or citrate. Such substrate may be oxidized for example to carbon dioxide and/or to further products, preferably products creating biomass.

In one embodiment, the substrate that is naturally metabolized by the organism may be converted into a valuable product, i.e. a value added product, in the sense of an end-product of a process of the invention. In another embodiment the substrate that is naturally metabolized by the organism may be reacted into an intermediate which is further reacted, as an intermediate product, in a method of the invention to obtain a valuable end product. For example, a substrate may be metabolized by one of the organisms, the photoautotrophic or the chemoheterotrophic organism, wherein the substrate in this case is a natural substrate, to create an intermediate product. Said intermediate product may then further be reacted by the other organism to obtain an end product. From the perspective of the other organism, the intermediate product may be a substrate, which may again be a substrate that can be naturally metabolized or a substrate that cannot be naturally metabolized.

In one embodiment, which may be employed, alternatively or additionally, the substrate is a substrate which is not naturally metabolized by the photoautotrophic microorganisms and/or the chemoheterotrophic microorganisms, wherein the ability of converting, particularly by oxidation, the substrate to a product, or the ability to catalyze a reaction of interest, was introduced into the photoautotrophic microorganisms and/or the chemoheterotrophic microorganisms by genetic modification.

Genetic modification to impart to the photoautotrophic microorganisms and/or the chemoheterotrophic microorganisms the ability to convert a substrate that is not a natural substrate for such organism, may be done by imparting to the microorganism the ability to express the gene for a suitable enzyme catalyzing the desired reaction.

The genetic modification may be the introduction of a heterologous nucleic acid molecule or a foreign nucleic acid molecule which leads to the gene expression of a suitable enzyme catalyzing the desired reaction. The heterologous nucleic acid molecule or a foreign nucleic acid molecule may encode a protein having the function of the enzyme catalyzing the desired reaction.

A foreign nucleic acid molecule is a nucleic acid molecule not naturally occurring in the microorganism, particularly the wild type microorganism, or a nucleic acid molecule that is present integrated at a site in the genome of the microorganism in which it does not occur in wild-type microorganism, i.e. in another genomic environment. A heterologous nucleic acid molecule is a nucleic acid molecule not naturally occurring in the microorganism, particularly not occurring in the wild type of the microorganism.

The heterologous nucleic acid molecule or a foreign nucleic acid molecule may be integrated into the DNA of the microorganism or not integrated and for example be located on a plasmid instead of the chromosome. The expression may be permanent expression or transient expression.

A large number of techniques are available, and known to the skilled person, for the introduction of DNA into a microorganism. These techniques include transformation by electroporation, transfection, triparental mating, conjugation or utilizing natural competence of cells (Molecular Cloning: A Laboratory Manual, by Michael R. Green, Joseph Sambrook, ISBN 978-1-936113-42-2; Mell J. et al., *Journal of Bacteriology*, Vol 96, 8, 2014, p. 1471-1483). Furthermore, genetic modification of the genome of the photoautotrophic organism and/or the chemoheterotrophic organism may be accomplished applying CrispCas (Wu, W. et al., (world wide web at ncbi.nlm.nih.gov/pubmed/30171624" \o "Medicinal research reviews.) 2018 Sep. 1. doi: 10.1002/med.21537; Behler et al., *Trends in Biotechnology*, doi: 10.1016/j.tibtech.2018.05.011), or gene knock-out/knock-in strategies via conjugative plasmids (Silva-Rocha R. et al., *Nucleic Acids Res.* 2013 January; 41 (Database issue): D666-75. doi: 10.1093/nar/gks1119. Epub 2012 Nov. 23).

Specific examples of substrates for conversion into a product include glucose, sucrose glycerol, lactose, hydrolyzed starch, D-alanine, whey permeate; aromatic hydrocarbons such as benzene, toluene, xylene, ethylbenzene, styrene, naphthalene, and phenanthrene; aliphatic hydrocarbons such alkanes, alkenes, alkynes, such as tridecane and tetradecane; alicyclic compounds such as cyclohexanone and cyclohexanol; heterocyclic compounds such as methylimidazole, collidine and picoline; higher fatty acids such as lauric acid, palmitic acid, stearic acid, oleic acid and linolic acid; higher alcohols, such as octyl alcohol, decyl alcohol, lauryl alcohol, cetyl alcohol and stearyl alcohol; fatty acid esters such as ethyl caprylate and ethyl caprylate; an aldehyde, a ketone.

An alkane may be for example oxidized to an alcohol, an alcohol to an aldehyde, a cyclic ketone to a lactone etc. Specific examples are:

Cyclohexane oxidation to cyclohexanol (catalyzed by cytochrome P450 enzyme)

$$C_6H_{12}+O_2+2H^++2e^-\rightarrow C_6H_{12}O+H_2O$$

Baeyer-Villiger oxidation of cyclohexanone to ε-caprolactone (catalyzed by cyclohexanone monooxygenase enzyme)

$$C_6H_{10}O+O_2+2H^++2e^-\rightarrow C_6H_{10}O_2+H_2O$$

In these examples, and generally, the ability of gene expression to the respective enzyme, cytochrome P450 or cyclohexanone monooxygenase, can be introduced into the photoautotrophic microorganisms and/or the chemoheterotrophic microorganisms by genetic modification.

These examples are not limiting and intended to illustrate the invention. Literature references concerning these examples are given, which are incorporated for reference. Some references are identified by doi numbers (Digital Object Identifier numbers) by the International DOI Foundation (IDF) (www.doi.org).

Suitable enzymes, whose gene expression can be initiated by genetic modification, are selected from:
Monooxygenases (MO) (doi: 10.1039/c3cs60011d.),
such as
styrene MO (Appl Environ Microbiol. 1998; 64:2032-43),
cyclohexane MO (Appl. Microbiol. Biotechnol. 2015; 99:6889-6897),
cyclohexanone MO (doi: 10.1002/bit.26469; WO 2018/046104),
xylene MO (Appl Environ Microbiol. 2002; 68:560-568),
alkane MO (world wide web at doi.org/10.1002/bit.25248),
methane MO (J. Am. Chem. Soc. 2016; 138:9327-9340)
cytochrome P450 monooxygenase (WO 2018/046104);
Dioxygenase (DO) (Tetrahedron 2003; 59:7075-7101),
such as
proline-4-hydroxylase (Microb Cell Fact 2015; 14:108),
toluene DO (J Bacteriol 1997; 179:3858-3865);
Dehydrogenases (DH),
such as alcohol DH,
more specifically
cyclohexanol DH (doi: 10.1002/bit.26469),
acetol DH (doi: 10.1002/bit.26468),
aldehyde DH,
more specifically methylglyoxal DH (doi: 10.1002/bit.26468),
lactonase (DOI: 10.1074/jbc.M311194200);
transaminases (world wide web at doi.org/10.1002/adsc.201200958);
methylglyoxal synthase (doi: 10.1002/bit.26468).

Possible reactions in the present invention which could be performed with above-mentioned enzymes are, without limitation For cyclohexane MO:

$$Cyclohexane+O_2+NADH+H^+\rightarrow Cyclohexanol+NAD^++H_2O$$

For cyclohexanone MO:

$$Cyclohexanone+O_2+NADPH+H^+\rightarrow \varepsilon\text{-caprolactone}+NADP^++H_2O$$

For xylene MO:

$$Toluene+O_2+NADH+H^+\rightarrow Benzylalcohol+NAD^++H_2O$$

For alkane MO:

$$Dodecanoic\ acid\ methyl\ ester+O_2+NADH+H^+\rightarrow Hydroxydodecanoic\ acid\ methyl\ ester+NAD^++H_2O$$

For methane MO:

$$Methane+O_2+NADH+H^+\rightarrow methanol+NAD^++H_2O$$

For Dioxygenase (DO), specifically proline-4-hydroxylase:

$$L\text{-proline}+\alpha\text{-ketoglutarate}+O_2\rightarrow Trans\text{-4-hydroxyproline}+succinate+CO_2$$

For toluene DO, $$toluene+NADH+H^++O_2\leftrightarrows(1S,2R)\text{-3-methylcyclohexa-3,5-diene-1,2-diol}+NAD+$$

For Dehydrogenases (DH), specifically alcohol (DH), more specifically cyclohexanol DH:

$$Cyclohexanol+NAD^+\rightarrow cyclohexanone+NADH+H^+$$

For acetol DH:

$$Acetol+NADPH+H^+\rightarrow 1,2\text{-propanediol}+NADP^+$$

For Dehydrogenases (DH), specifically aldehyde (DH), more specifically methylglyoxal DH:

$$methylglyoxal+NADPH\rightarrow acetol+NADP^+$$

Others:
Lactonase: lactone+$H_2O\rightarrow\omega$-hydroxyacid
Specific example: ε-caprolactone+$H_2O\rightarrow$6-hydroxyhexanoic acid
transaminases:
organic acid+aminoacid$\rightarrow$aminoacid+organic acid;
specific example: 6-oxohexanoic acid+alanine$\rightarrow$6-aminohexanoic acid+pyruvate
methylglyoxal synthase:
dihydroxyacetone phosphate$\rightarrow$methylglyoxal+$P_i$ The biofilm comprises the photoautotrophic microorganisms, the chemoheterotrophic microorganisms and extracellular polymeric substances (EPS). The photoautotrophic microorganisms and the chemoheterotrophic microorganisms may be partially or wholly embedded in EPS. EPS are secreted by the photoautotrophic microorganisms and/or the chemoheterotrophic microorganisms. EPS may comprise one or more of a substance that is selected from polysaccharides, proteins, lipids, and DNA.

The biofilm may be a biofilm which is obtained by cultivation of a mixture of the photoautotrophic microorganisms and the chemoheterotrophic microorganisms, particularly on a surface.

In one embodiment, the thickness of the biofilm is from about 10 μm up to about 500 μm. The thickness of the biofilm may vary The photoautotrophic microorganisms may be prokaryotic microorganisms or eukaryotic microorganisms or cells.

The chemoheterotrophic microorganisms may be prokaryotic microorganisms or eukaryotic microorganisms or cells.

In one embodiment, the photoautotrophic microorganisms are selected from the group consisting of an algae and/or a cyanobacterium. In a more specific embodiment the photoautotrophic microorganisms are selected from the genus *Synechocystis*, particularly *Synechocystis* sp. PCC 6803 (Pasteur Culture Collection accession No. PCC 6803).

In one embodiment, the chemoheterotrophic microorganisms are selected from bacteria. In a more specific embodiment the chemoheterotrophic microorganisms are selected from the genus *Pseudomonas*, particularly *Pseudomonas* sp. VLB120, more specifically *Pseudomonas taiwanensis* VLB120_pCom10_capro (Deutsche Sammlung von Mikroorganismen und Zellkulturen, DSMZ accession No. DSM 32333), or *Pseudomonas taiwanensis* VLB120ΔC (Deutsche Sammlung von Mikroorganismen und Zellkulturen, DSMZ accession No. DSM 24711).

In one embodiment, the biofilm is adhered to a surface of a carrier. Preferably, the biofilm is produced, or grown, on the carrier. The carrier is preferably an artificial carrier. An artificial carrier is either man-made or based on a natural carrier which is modified by an artificial (i.e. man-made) process. The carrier may be made from numerous substances, wherein particularly suitable substances are glass, ceramic, plastic metal, or a combination thereof.

The carrier may be made from a translucent, i.e. light-transmissive, material.

The shape of the carrier is not particularly restricted. In one embodiment, the carrier is selected from a flat carrier, a tube or a capillary. In case of a tube or a capillary the biofilm is preferably located on an inner surface. The carrier may be a part of the reactor which is described hereinafter. For example, the carrier may be a reaction vessel, a reaction tube, or a capillary.

Light may be any light that is suitable to provide energy for photoautotrophic microorganisms, particularly to induce photosynthesis, even more particularly to induce photosynthetic water oxidation. Light may be visible light, such as daylight. Possible light spectra are given in A. Hoschek et al., Angew Chemie Int Ed 2017; 56:15146-15149, which is incorporated by reference.

The Reactor:

The reactor of the invention may comprise any of the compositions of the invention that are described in this specification. It is explicitly referred to the disclosure of any other aspects of the invention which could also applied in the reactor of the invention or when using the reactor.

The reactor may also be called a "biofilm-reactor". The reactor may comprise the carrier described before, the carrier comprising the biofilm on the surface of the carrier. In this case the surface of the carrier may be mentioned surface of the reactor, particularly an inner surface. An inner surface means a surface which is located inside of the reactor, particularly within a room or volume of the reactor wherein the reaction is happening.

The reactor is preferably designed in a way that the composition, particularly the biofilm, can be illuminated or irradiated with light. The reactor may be designed in a way that light can be guided or conducted to the biofilm. This can be reached by different means. Light conducting means can be used. A further possibility is that the surface on which the biofilm is located is translucent, or that a carrier on which the biofilm is located, or any other part of the reactor on whose surface the biofilm is located is translucent. Light can then be irradiated through the surface, the carrier, or the part of the reactor.

In one embodiment, the reactor is a capillary reactor, comprising at least one capillary member, wherein the biofilm adheres to an inner surface of at least one capillary member, and wherein the capillary member is made from a translucent, i.e. light-transmissive, material, such as light-transmissive glass or plastic. In such capillary reactor, multiple capillaries may be present, for example arranged in parallel fashion. Liquid medium and/or gaseous medium may be flown through the capillary to be contacted with the biofilm. The liquid medium and/or gaseous medium may comprise one or more of the following components: water, carbon source for the photoautotrophic and/or the chemoheterotrophic microorganisms, substrate (educt) to be reacted to a desired product, minerals, trace elements, nitrogen source, buffer salts, inducer and vitamins.

A reactor which can be used in the present invention, provided that a composition of the invention is incorporated in the reactor, is described in patent application WO 2012/152337 A1, whose content is incorporated by reference in this application.

The reactor may comprise at least one capillary member, at least one reservoir for at least one liquid phase, and at least one reservoir for a gaseous phase, wherein the at least one reservoir for a liquid phase and the at least one reservoir for a gaseous phase are in interruptible fluid connection with the at least one capillary member.

The at least one capillary member provides a support for a biofilm that has to be established in the reactor for converting a substrate to a product. Hence, the biofilm within the at least one capillary constitutes the biocatalyst for converting the substrate to the product. Said biofilm is established and thus present on the inner surface of the capillary member when the biofilm reactor is in operating condition.

The capillary member or at least one capillary member of the biofilm reactor of the present invention may for example be configured as a tube or as a pipe. Any suitable combination of tubes and pipes can be utilized too. The at least one capillary member may be a tube, preferably selected from the group consisting of porous tubes, non-porous tubes, photopermeable tubes, transparent or translucent tubes, hydrophobic tubes, and hydrophilic tubes. Photopermeable tubes are permeable to photoradiation of proper wavelengths. Transparent or translucent tubes are adequately permeable to visible radiations to allow the human eye to see through it.

The at least one capillary member may have any suitable cross-section. The at least one capillary member may have a round cross-section, a square cross-section, a rectangular cross-section or a triangular cross-section. Preferably, the at least one capillary member of the biofilm reactor has a round or circular cross-section.

The dimensions of the at least one capillary member can be varied in a wide range, depending on—for example—the peculiar needs for each species of microorganism constituting the biofilm, for each type bioconversion reaction to be carried out, for the different compositions of the different phases to be utilized, the efficiency of the bioconversion reaction to be performed, and the desired or required flow rate of the phases. The inner diameter of the at least one capillary member is preferably less than 5 mm, more preferably less than 4 mm, and most preferably less than 3 mm. The at least one capillary member is preferably at least 0.5 mm in inner diameter, preferably at least 2 mm. In a particularly preferred embodiment, the at least one capillary member has an inner diameter of between 0.5 mm and 2.5 mm. In addition, it is preferred that the at least one capillary member has a length of between 0.01 m and 2.5 m.

The at least one capillary member may comprise an inlet opening and an outlet opening. The inlet opening of the at least one capillary member is in fluid connection with reservoirs for each of the phases, the at least one liquid phase, and the at least one gaseous phase such that the different phases can flow through the at least one capillary member in direction from its inlet opening to its outlet opening. The fluid connection of the at least one capillary member and the reservoirs for each of the phases is interruptible such that the flow of each phase through the at least one capillary member can be interrupted separately. The phases which may flow through the at least one capillary member of the biofilm reactor can leave the at least one capillary member at their outlet opening. The phases leaving the at least one capillary member may be collected, separated from each other and/or analyzed for their composition and/or recycled back into the system. The desired product may be separated from the phase it is contained in by suitable means.

The biofilm reactor of the present invention comprises at least one reservoir for at least one liquid phase. At least one of said at least one liquid phases may be an aqueous phase, and/or at least one of said liquid phases may be an organic phase. Hence, the biofilm reactor comprises at least one reservoir for at least one liquid aqueous phase, and/or at least one reservoir for at least one liquid organic phase. The at least one liquid aqueous phase may be selected from the group consisting of minimal media, complete media, waste water, and mixtures thereof. The at least one organic phase may be selected from the group consisting of include alkanes, isoparaffins, n-alkylbenzenes, isoalkylbenzenes, alicyclic hydrocarbons, ethers, aliphatic esters, silicone oils, aromatic hydrocarbons, aliphatic hydrocarbons, heterocyclic compounds, higher fatty acids, higher alcohols, phthalates or mixture of phthalates and fatty acid esters.

The biofilm reactor of the present invention may comprise at least one reservoir for at least one gaseous phase. The gaseous phase may consist of a gas or a mixture of gases. The gaseous phase is preferably selected from the group consisting of air, oxygen, noble gases, carbon dioxide, carbon monoxide, sulfur dioxide, nitrogen, hydrogen sulfide, methane, butane, volatile organic molecules, and other gases.

It is to be understood that each of the reservoirs for the at least one liquid phase and the at least one gaseous phase may comprise one, two or a multiple number of reservoir chambers which are in fluid connection with one another. It is also to be understood that the at least one reservoir for the gaseous phase does not necessarily have to comprise one or more reservoir chambers. Instead, ambient air can be utilized as gaseous phase.

As all phases shall be supplied to the biofilm reactor in sterile form, microbes might have to be removed from the phases or have to be destroyed before the phases enter the biofilm before gaining access to the biofilm catalyst. Hence, the biofilm reactor may comprise suitable means for sterilizing at least one of the phases before said phase will enter the capillary member. Such suitable means for sterilizing at least one of the phases may preferably be at least one filter. Filters are particularly preferred for sterilizing the gaseous phase, and filters are preferred above all if the gaseous phase is ambient air. Usually, liquid phases will be supplied to their reservoirs in sterile condition, and do not necessarily require additional means for their sterilization. Means for sterilizing liquid media such as filters, means for irradiating the liquid medium, and means for heat sterilization of the liquid medium are known to the skilled person.

Each reservoir comprises at least one outlet. At least one outlet of each reservoir is in fluid connection with the inlet of the at least one capillary member. Preferably, the fluid connection of the reservoirs with the at least one capillary member is mediated by conduits. The conduits may be selected from the group consisting of pipes and tubes, preferably flexible tubes. Each pipe or tube is resistant to at least the ingredients constituting the phase flowing through the respective pipe or tube. Resistance of the conduit to the compounds of the phase flowing through this conduit is of particular importance for the conduit which connects the at least one reservoir for the at least one liquid organic phase with the at least one capillary member.

The biofilm reactor of the present invention may further comprise at least one means for generating a segmented flow of the at least one liquid phase and the at least one gaseous phase from the respective reservoirs through the conduits connecting each reservoir with the at least one capillary member, and through the at least one capillary member. Said means for generating a segmented flow can be selected from the group consisting of pumps and valves. In one embodiment, each reservoir is in fluid connection with the at least one capillary member by a separate conduit, wherein each conduit is provided with a separate pump, or with a single channel of a multi-channel pump. Preferably, said conduits are tubes and are provided with a peristaltic or a piston pump. The biofilm reactor of the present invention can provide a segmented flow of the at least one liquid phase and the at least one gaseous phase through the at least one capillary member. Therefore, the biofilm reactor comprises at least one means for segmenting the flow of phases, e. g. at least one means for interrupting an otherwise continuous flow of the phases. Said means for segmenting the flow of the phases can be selected from the group consisting of pumps, fittings, valves, and combinations of pumps and valves, and pumps and fittings. In a preferred embodiment, the biofilm reactor comprises at least one pump, more preferably at least one peristaltic pump. In another or additional embodiment, the biofilm reactor comprises at least one three way valve or at least one four way valve. Said three way valve or said four way valve is actable/operable such that it is adjustable which reservoir provides the supply of a phase for the capillary member.

The biofilm reactor may further comprise means for maintaining a predetermined temperature in the at least one capillary member. The means for maintaining a predetermined temperature in the at least one capillary member may for example be a basin through which the at least one capillary member runs, the basin comprising a medium having the predetermined temperature. This embodiment has the advantage that the temperature of the biofilm can be adjusted and maintained in an optimal range for growth and propagation of the biofilm, and/or for bioconversion. In a particular embodiment, wherein the at least one capillary member is a porous tube, the medium within the basin may consist of or may comprise the substrate for bioconversion, which substrate may access the biofilm biocatalyst through the porous wall of the at least one capillary member. When the capillary member is a porous tube, such tube can also be utilized for extraction of super saturated oxygen.

In an embodiment, the biofilm reactor comprises at least one capillary member, one reservoir for a liquid phase, preferably a liquid aqueous phase, and one reservoir for a gaseous phase, wherein the reservoir for the liquid phase and the reservoir for the gaseous phase are in interruptible fluid connection with the at least one capillary member.

In its operating mode, two different phases, a liquid phase and a gaseous phase, are flowing through the at least one capillary. In a preferred embodiment the at least one capillary consists of a material that is resistant to the ingredients that are present in the different phases, that is non-toxic to the microorganisms for forming the biofilm, and that permits the microorganisms for forming the biofilm to adhere thereon. In an alternative embodiment, the at least one capillary is provided with a coating on its inner surface, wherein the coating is resistant to the ingredients that are present in the different phases, is non-toxic to the microorganisms for forming the biofilm, and permits the microorganisms for forming the biofilm to adhere to the coated inner surface of the capillary. It is to be understood that a biofilm reactor of the invention may comprise at least one capillary made of a material that is resistant to the ingredients that are present in the different phases, that is non-toxic to the microorganisms for forming the biofilm, and that permits the microorganisms for forming the biofilm to adhere thereon, or at least one capillary comprising a coating on its inner surface, wherein the coating is resistant to the ingredients that are present in the different phases, is non-toxic to the microorganisms for forming the biofilm, and permits the microorganisms for forming the biofilm to adhere to the coated inner surface of the capillary. In another embodiment, of the present invention, the biofilm reactor comprises at least one capillary, at least one reservoir for a liquid aqueous phase, at least one reservoir for a liquid organic phase, and at least one reservoir for a gaseous phase, wherein the at least one reservoir for a liquid aqueous phase, the at least one reservoir of the liquid organic phase, and the at least one reservoir for the gaseous phase are in fluid connection with the at least one capillary.

In its operating mode, one or more different phases, in any combination, can flow through the at least one capillary, the phases being selected from the aqueous phase, the gaseous phase, and the organic phase.

Hence, at least the inner surface of the at least one capillary has to be resistant to the ingredients that are present in the different phases, i.e. the at least one aqueous phase, the at least one organic phase, and the at least one gaseous phase. In addition, the inner surface of the at least one capillary has to be non-toxic to the microorganisms constituting the biofilm on the inner surface of the capillary. Moreover, the inner surface of the at least one capillary has to permit the microorganisms to adhere to said inner surface such that a biofilm can be established thereon. Thus, in a preferred embodiment the at least one capillary consist of a material that is resistant to the ingredients that are present in the different phases, that is non-toxic to the microorganisms for forming the biofilm, and that permits the microorganisms for forming the biofilm to adhere thereon. In an alternative embodiment, the at least one capillary is provided with a coating on its inner surface, wherein the coating is resistant to the ingredients that are present in the different phases, is non-toxic to the microorganisms for forming the biofilm, and permits the microorganisms for forming the biofilm to adhere to the coated inner surface of the capillary. It is to be understood that a biofilm reactor of the invention may comprise at least one capillary made of a material that is resistant to the ingredients that are present in the different phases, that is non-toxic to the microorganisms for forming the biofilm, and that permits the microorganisms for forming the biofilm to adhere thereon, and at least one capillary comprising a coating on its inner surface, wherein the coating is resistant to the ingredients that are present in the different phases, is non-toxic to the microorganisms for forming the biofilm, and permits the microorganisms for forming the biofilm to adhere to the coated inner surface of the capillary.

The Method for Reacting a Substrate

In the method of the invention for reacting a substrate, any composition of the invention and or any reactor of the invention could be employed. It is explicitly referred to the previous disclosure. In the method, the biofilm of the composition of the invention is contacted with the substrate which is to be reacted. The reaction in the method may be an oxidation reaction.

The method can be used to produce valuable chemicals.

One example of valuable chemicals are so-called "platform chemicals". Platform chemicals are produced on a substantial scale (up to million tons per annum) but at meager costs 1-2 €/kg. The chemical process is the state-of-art for the platform chemicals. Although most of the biological processes are sustainable for platform chemical production as compared to the chemical process, high production cost limits commercial exploitation of bioprocess. One of the reasons for high production costs is the expensive raw materials. Glucose is a standard carbon and electron source used in many biological processes. However, glucose is expensive (0.4-0.5 €/kg) and its utilization as a carbon and electron source limits production of (platform) chemicals that are below 1-2 €/kg. In addition to raw material costs, bioprocesses of the prior art are energy intensive for maximizing the mass transfer of oxygen and $CO_2$ extraction which contributes to production costs. Photosynthetic microorganisms utilize $CO_2$ as the carbon source and water as the sole electron donor for the production of biomass and also for biological reactions. These raw materials are cheaper compared to glucose and an economically attractive option for bioprocess development. For the economic feasibility of phototrophic bioprocess, following consideration needs to be taken into account. The cost of photobioreactors should be below 40 €/$m^2$, the energy demand for mixing and gas transfer should not exceed 50 W/$m^3$, and the biomass concentration has to be at least greater than 20 $g_{CDW}$/L. The current invention achieves these criteria by utilizing above-mentioned mixed species biofilm concept and developing a continuous phototrophic process that is cost effective, has a low energy demand, and retains high biomass.

A further example of valuable chemicals are fine chemicals, specialties, or pharmaceuticals. Such chemicals are usually sold with a high price and on a lower scale.

Possible reactions of interest for a method of the invention were already mentioned above when describing the composition of the invention and reaction of a substrate to a product. The product may be selected from the group consisting of an alcohol, a lactone, a polylactone, an aldehyde, a ketone, a carboxylic acid, a dicarboxylic acid, an aminohexanoic acid, a steroid, a peptide, a polyketide, a microcystin, a gaseous product such as hydrogen, methane, ethene.

When exposing the composition to light, production of oxygen by photosynthetic water oxidation is initiated. The composition is also brought into contact with water.

In any case, at least some of the oxygen produced by the photoautotrophic microorganism is respired by the chemoheterotrophic microorganism.

The produced oxygen may be used to oxidize the substrate, which is preferably an organic compound. An oxidized product which is a product of interest, or a valuable product, is obtained.

Alternatively or additionally, the produced oxygen may be used for a natural metabolism in the chemoheterotrophic microorganism, such as for oxidation of a natural substrate.

The method may comprise adding a source of inorganic carbon, such as carbonate or carbon dioxide, which is naturally metabolized by the photoautotrophic microorganisms.

It is to be understood, that in this method, or any other method of the invention, a suitable (culture) medium may be employed. The medium may constitute a liquid phase in a method of the invention. A suitable medium comprises ingredients for growing and/or maintaining mentioned microorganisms or mentioned biofilm. Ingredients may be selected from one or more of the following: minerals, trace elements, nitrogen source, buffer salts, inducer and vitamins. Further possible ingredients, like an inorganic carbon source, are mentioned at other place in this description. Suitable media are known to the skilled person and exemplified in the examples section.

In one embodiment of the method, the method further comprises
- adding or providing a further substrate which is naturally metabolized by the chemoheterotrophic microorganisms, preferably if the substrate that is reacted to the product (which is the desired product) is a substrate which is not naturally metabolized by the chemoheterotrophic microorganisms.

This embodiment may be beneficially used if the substrate that is reacted to the product is a substrate which is not naturally metabolized by the chemoheterotrophic microorganisms. Then, the substrate which is naturally metabolized may additionally be added, as a further substrate. It may then be called a "second substrate" or "natural substrate".

In this embodiment, a natural substrate is added which is consumed by the chemoheterotrophic microorganisms in a metabolic process. Adding the natural substrate promotes growth of the chemoheterotrophic microorganisms, which may be a tool to influence the ratio of chemoheterotrophic microorganisms to photoautotrophic microorganisms. If the catalytic activity to convert a substrate to a product (of interest) is solely or mainly contained in the chemoheterotrophic microorganisms, increasing the number of chemoheterotrophic microorganisms is beneficial.

In one embodiment of the method the reactor is a capillary reactor as described above, the method further comprising passing segments of a gaseous phase and segments of a liquid phase alternatingly through the capillary member, wherein
- the gaseous phase and/or the liquid phase comprises the substrate (which is converted to the desired product), and, if used, above-mentioned further substrate,
- the gaseous phase and/or the liquid phase takes up the product, and optionally oxygen that is produced by the photoautotrophic microorganisms.

The gaseous phase and/or the liquid phase may further comprise said source of inorganic carbon, such as carbonate or carbon dioxide, which is naturally metabolized by the photoautotrophic microorganisms.

The benefit of oxygen uptake is that oxidative stress on organisms in the biofilm can be reduced. Depending on the ratio of photoautotrophic microorganisms to chemoheterotrophic microorganisms, excess oxygen may be produced by photoautotrophic microorganisms which is not consumed by chemoheterotrophic microorganisms. This may for example be the case when no substrate which is naturally metabolized by the chemoheterotrophic microorganisms is added and the ratio of photoautotrophic microorganisms to chemoheterotrophic microorganisms is rather high.

In the method of the invention the mentioned embodiments
a) adding or providing a further substrate which is naturally metabolized by the chemoheterotrophic microorganisms, preferably if the substrate that is reacted to the product is a substrate which is not naturally metabolized by the chemoheterotrophic microorganisms,
b) passing segments of a gaseous phase and segments of a liquid phase alternatingly through the capillary member may be employed alternatively or additionally.

Alternative employment has the advantages already mentioned. Employing embodiment b) in addition to a) may have one or more of the following advantages:
- segments of a gaseous phase prevent clogging in the capillary,
- segments of a gaseous phase may carry the substrate that is converted in the process to a valuable product,
- segments of a gaseous phase may limit further increase of the biofilm. If thickness of the biofilm is too high, the reaction of interest may be limited too much by mass transport,
- segments of a gaseous phase leading to a higher uptake of substrate which is naturally metabolized by the chemoheterotrophic microorganisms, which is assumed to happen because of fluidic stress and (aqueous-air) interfacial stress that is imparted on the chemoheterotrophic microorganisms. Higher uptake of substrate may lead to increased production of extracellular polymeric substance which may stabilize the biofilm from high fluidic and interfacial stresses.

In the above-described embodiment of a method of the present invention the expression of "segments of a gaseous phase and segments of the at least one of a liquid phase are flown through the capillary member in alternatingly fashion" means that a segment of a gaseous phase is followed by a segment of a liquid phase and vice versa. This is also called "segmented flow". Volume segments of gaseous phase and volume segments of a liquid phase are different phases which are flowing through the at least one capillary member in a segmented fashion.

The at least one liquid phase may be a liquid aqueous phase or a liquid organic phase. Both of liquid aqueous phase and a liquid organic phase may be employed. Thus, the liquid phase may also comprise a combination of at least one liquid aqueous phase and at least one liquid organic phase.

More specifically, the method comprises conversion of a substrate to a product by a biofilm catalyst which is present on the inner wall of at least one capillary member within a capillary reactor which has been described herein before. In an embodiment of the method, the biofilm is subjected to a segmented flow of at least one liquid aqueous phase and at least one gaseous phase, wherein the segments of the at least one liquid phase and the at least one gaseous phase possess a segmented flow through the at least one capillary member. In another embodiment of the method, the biofilm is subjected to a segmented flow of at least one liquid aqueous phase, at least one liquid organic phase, and at least one gaseous phase, wherein the segments of the at least one liquid aqueous phase, the at least one liquid organic phase and the at least one gaseous phase possess a segmented flow through the at least one capillary member, i.e. the different phases employed are flowing through the at least one capillary member in a segmented fashion.

The method may comprise the step of establishing the biofilm on the inner surface of the at least one capillary member. The method also comprises maintaining the biofilm on the inner surface of the at least one capillary member, in particular during the bioconversion of the substrate to the product (value added product, desired product, product of choice).

The liquid aqueous phase is preferably a medium containing all ingredients that are required by the microorganisms for growth and propagation for constituting a biofilm. The liquid aqueous phase can be selected from the group consisting of minimal media, complex media, and waste water. Each species of microorganisms that may be employed as biofilm biocatalyst in the segmented flow biofilm reactor of the present invention and/or in the method according to the present invention for converting a substrate to a product, is preferably provided with the medium said microorganisms prefer. A wide variety of media are available for the skilled artisan for obtaining optimal multiplication and/or bioconversion performance. The different media may for example differ in the carbon source supplied to the biofilm biocatalyst, e.g. glucose, glycerol, citrate, etc. In a special embodiment, the aqueous phase consists of M9-medium. The liquid aqueous medium may contain the substrate that shall be converted to a product when the biofilm was established on the inner surface to the at least one capillary member.

The liquid organic phase may consist of or comprise a substrate, particularly an organic substrate, to be converted. An organic substrate may be dissolved in an organic solvent, and the resulting organic solution may be employed as organic phase. Examples for organic solvents that may be employed for the organic phase may be selected from the group consisting of alkanes, isoparaffins, n-alkylbenzenes, isoalkylbenzenes, alicyclic hydrocarbons, ethers, aliphatic esters, silicone oils, aromatic hydrocarbons, aliphatic hydrocarbons, heterocyclic compounds, higher fatty acids, higher alcohols, phthalates and mixtures of phthalates and fatty acid esters. In addition, a pure organic phase may consist of the organic substrate to be converted.

The substrate which is reacted in the method of the invention to a product may be soluble in the liquid aqueous phase. Then the substrate may be incorporated into the liquid aqueous phase when the biofilm has been established and shall be used for the bioconversion of said substrate. In cases of organic substrates which are only slightly soluble or insoluble in a liquid aqueous phase, the substrate can be dissolved in an organic solvent.

The gaseous phase consists of a gas or a mixture of gases. Suitable gases are selected from the group consisting of air, oxygen, noble gases, carbon dioxide, carbon monoxide, sulfur dioxide, nitrogen, hydrogen sulfide, methane, butane, volatile organic molecules, and other gases. The gaseous phase may be chosen according to the microorganisms requirements. The gaseous phase may consist of or comprise a gaseous substrate for the bioconversion such as, for example cyclohexane in gaseous form. Suitable temperature may be employed in order to transport a substrate in the gas phase.

The length of the segments of the different phases within the capillary may be up to 12 cm. In particularly preferred embodiments, the length of each segment is in a range of between 1 and 15 mm. The length of all segments or of the segments of two phases may be the same, or the lengths of all segments may differ from one another.

The volume of the segments of the different phases may be close to the total reactor volume. In a particularly preferred embodiment, the volume of the segments of each phase is in the range of between 1 and 15 µl. The volume of all segments or of the segments of two phases may be the same, or the lengths of all segments may differ from one another.

Depending on the diameter of the capillary, the volume of the segments determines the length of the segments. The flow rate of the segments/phases in the capillary may be in the range of 10-5,000 µl/min and preferably 50-1,000 µl/min (total flow rate).

The product of the method of the invention may be gaseous, hydrophilic or hydrophobic.

Use of a Composition of the Invention

In a further aspect, the invention relates to the use of a composition of the invention, or a reactor of the invention for cultivation of photoautotrophic microorganisms and/or chemoheterotrophic microorganisms or as microbial catalyst in the production of a chemical. The chemical may be a product of a method of the invention, particularly a valuable product. Further specific uses were mentioned in the description of the composition of the invention or the reactor of the invention.

Method for Producing a Composition of the Invention

In a further aspect, the invention also relates to a method for producing a composition of the invention, particularly for producing a biofilm comprising photoautotrophic microorganisms, chemoheterotrophic microorganisms, and components which are secreted by the photoautotrophic microorganisms and/or the chemoheterotrophic microorganisms, the method comprising:

cultivating a mixture of photoautotrophic microorganisms and chemoheterotrophic microorganisms, particularly on a surface.

In this method a biofilm is produced, the biofilm comprising the photoautotrophic microorganisms, the chemoheterotrophic microorganisms, and components which are secreted by the photoautotrophic microorganisms and/or the chemoheterotrophic microorganisms.

With respect to this method, and the terms used, and features mentioned, it is referred to the whole disclosure herein. Particularly, any composition of the invention can be employed in or produced with this method. Particularly, the surface may be a surface of a carrier disclosed herein. The surface may be a surface of or in a reactor. Particularly, the surface may be an inner surface of a capillary or a tube. Cultivation may be done inside of a capillary or a tube.

The method for producing a composition of the invention may be used for creating, preparing or conditioning a reactor of the invention, the reactor comprising the composition of the invention.

In this method, any method steps disclosed in this disclosure also with respect to other methods can be employed.

In a particular embodiment, the method for producing a composition of the invention comprises exposing the mixture to light.

The method for producing a composition of the invention may comprise adding a substrate which is naturally metabolized by the chemoheterotrophic microorganisms.

The method may comprise adding a source of inorganic carbon, such as carbonate or carbon dioxide, which is naturally metabolized by the photoautotrophic microorganisms.

The method may be performed in a capillary reactor as described herein. Then, the method may further comprise passing segments of a gaseous phase and segments of at least one of a liquid phase through the capillary member, as already described, wherein segments of a gaseous phase and segments of the at least one of a liquid phase flow through the capillary member in alternatingly fashion. The gaseous phase and/or the liquid phase may take up oxygen that is produced by the photoautotrophic microorganisms. The gaseous phase and/or the liquid phase may comprise a substrate which is naturally metabolized by the chemoheterotrophic microorganisms.

The gaseous phase and/or the liquid phase may comprise a source of inorganic carbon.

Cultivation may be done at suitable temperature, for example room temperature.

Cultivation may be done by using a suitable culture medium. A huge number of culture media are known to the skilled person, examples mentioned in this description and the examples. The liquid phase mentioned above may comprise or consist of culture medium.

Cultivation on a surface may be done by one or a combination of following steps:
 a) by contacting a mixture of photoautotrophic microorganisms and chemoheterotrophic microorganisms, preferably in liquid culture medium, with a surface, without or substantially without flow of the medium relative to the surface, and/or
 b) in a continuous mode, by flowing liquid culture medium relative to the surface, wherein the liquid culture medium may comprise a mixture of photoautotrophic microorganisms and chemoheterotrophic microorganisms.

Step a) is called an inoculation step. Then, microorganisms can adhere to the surface. Step a) may, without limitation, be performed for about 1-48 h, preferably 5-24 h.

During step b) the biofilm is grown further. Further microorganisms may be delivered or not. This step may be performed for some days, for example 1-12 days. If in step b) the liquid culture medium does not comprise a mixture of photoautotrophic microorganisms and chemoheterotrophic microorganisms, steps a) and b) are preferably done.

If the method shall comprise passing segments of a gaseous phase and segments of at least one of a liquid phase through the capillary member, wherein these segments flow through the capillary member in alternatingly fashion, the method may further comprise
 c) introducing segments of a gaseous phase thereby creating a flow of segments of a gaseous phase and segments of the liquid phase in alternatingly fashion. If no further liquid phase than the culture medium is introduced, the segments of the liquid phase are segments of the culture medium.

The method for producing a composition of the invention may be combined with a method of the invention for reacting a substrate to a product. Then the biofilm may first be formed and then the method of the invention for reacting a substrate, i.e. the method of bioconversion, may be performed.

The method of the invention for reacting a substrate may comprise inducing gene expression of the gene of interest, particularly when the the ability of converting the substrate was introduced into the chemoheterotrophic and/or photoautotrophic microorganisms by genetic modification. This leads to the production of an enzyme of interest, catalyzing the desired reaction. A further step of starting the method of the invention for reacting a substrate is delivery of the substrate, a step already mentioned in the method. Delivery of the substrate may be done some time after inducing gene expression mentioned above, preferably 1-3 days after.

A combined method for producing a composition of the invention and for reacting a substrate may comprise:
 cultivating a mixture of photoautotrophic microorganisms and chemoheterotrophic microorganisms, particularly on a surface, thereby producing a composition of the invention,
 contacting the composition with the substrate,
 exposing the composition to light,
 reacting the substrate to obtain a product.

The method may comprise, in any combination, steps and means that were disclosed for the single methods.

BRIEF DESCRIPTION OF THE FIGURES

Reference Symbols in the Figures are explained in the List of Reference Symbols.

BRIEF DESCRIPTION OF THE SEQUENCES IN THE SEQUENCE LISTING

Figure 1:
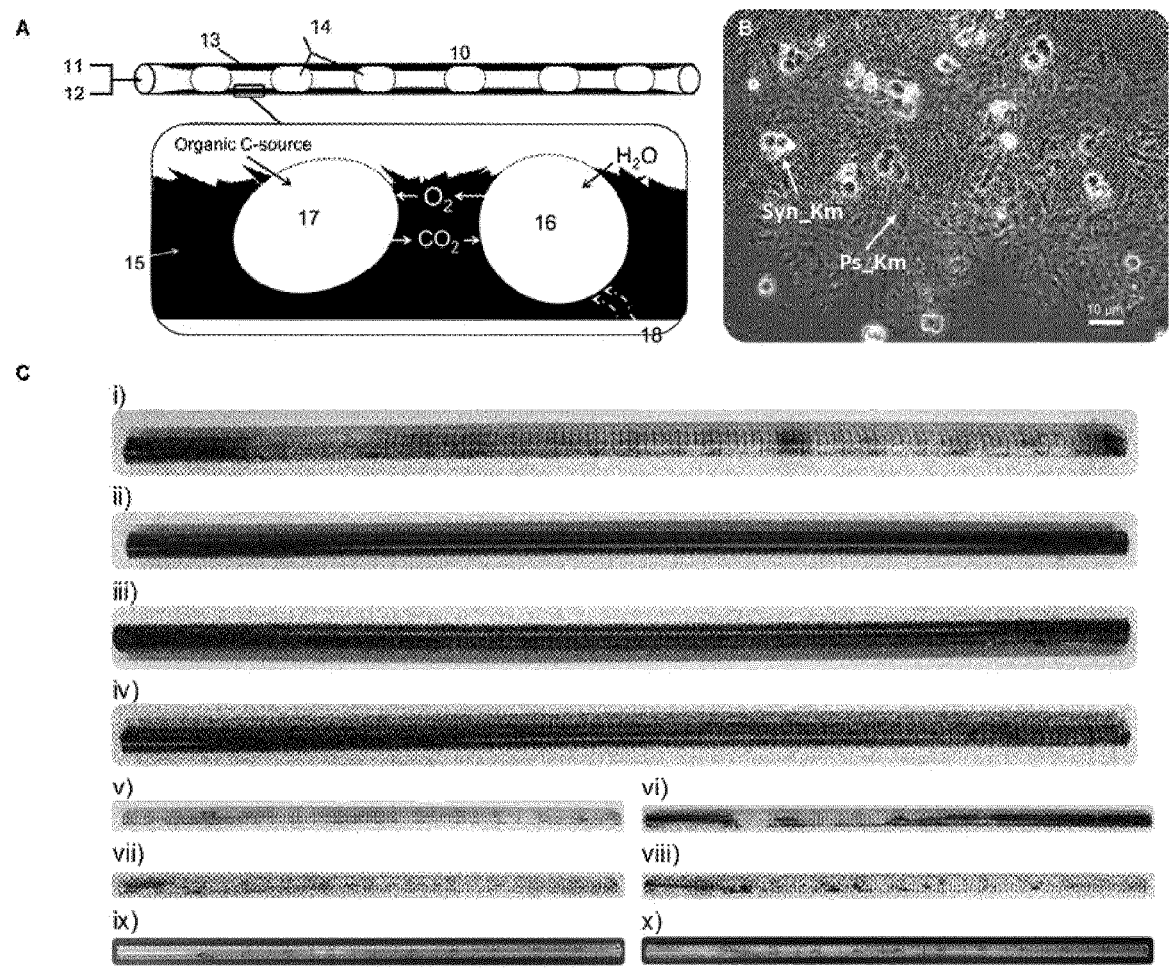
FIG. 1:
(A) Top: Scheme of a segmented-flow capillary reactor. Bottom: Basic principle of proto-cooperation between two microbial species with complementary metabolic activities (chemoheterotrophic and photoautotrophic). Cells of both species are embedded in extracellular polymeric substances and form a three-dimensional biofilm on the inner surface of the capillary. $O_2$ respiration (chemoheterotrophic strain) and $O_2$ evolution (photoautotrophic strain) balance the $O_2$ environment.
(B) Microscopic image of a mixed-species biofilm containing *Synechocystis* sp. PCC 6803_Km (Syn_Km) and *Pseudomonas* VLB120_Km (Ps_Km), harvested from a capillary reactor. Scale bar equal to 10 µm. (C) Pictures of capillary reactors taken five weeks after inoculation. Syn_Km=*Synechocystis* sp. PCC 6803_Km, Ps_Km=*Pseudomonas* VLB120_Km, w/o=without
Figure 2:
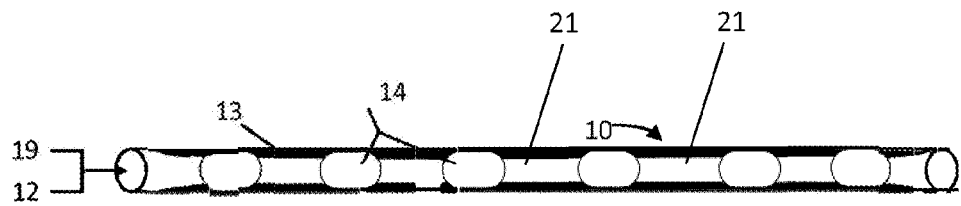
FIG. 2:
(A) Scheme of biofilm-based capillary reactor.
(B) Schematic representation of proto-cooperation and cyclohexane oxidation reaction within mixed-species biofilm containing *Synechocystis* sp. PCC 6803_CHX and *Pseudomonas* sp. VLB120_CHX.
(C) Demonstrating application of the concept looking at continuous cyclohexanol production at the capillary outlet. The activity is depending on the availability of light.
Figure 2:
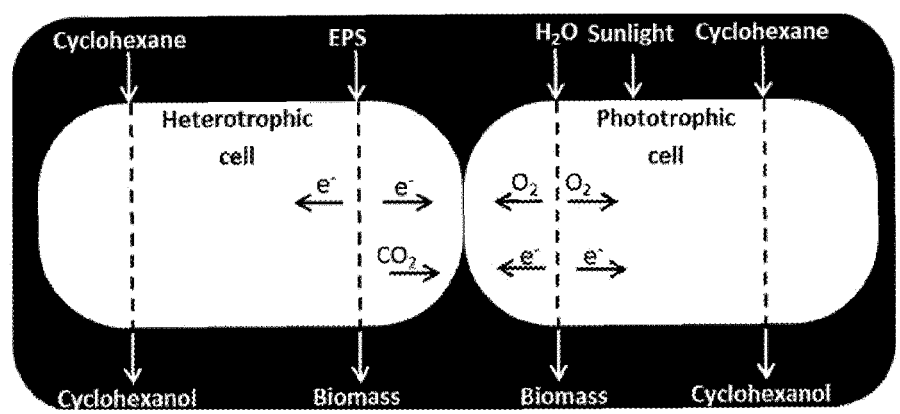
Figure 2:
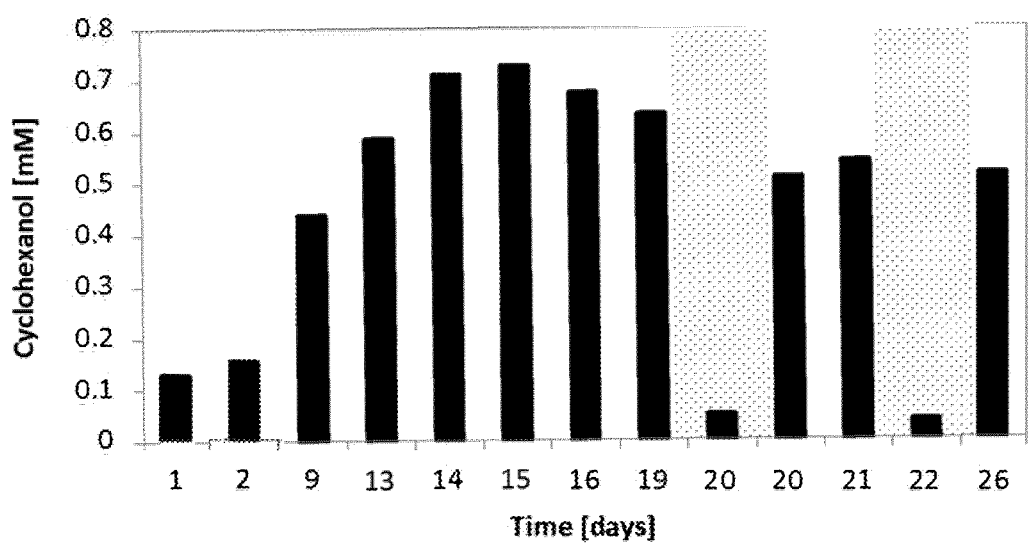
Figure 3:
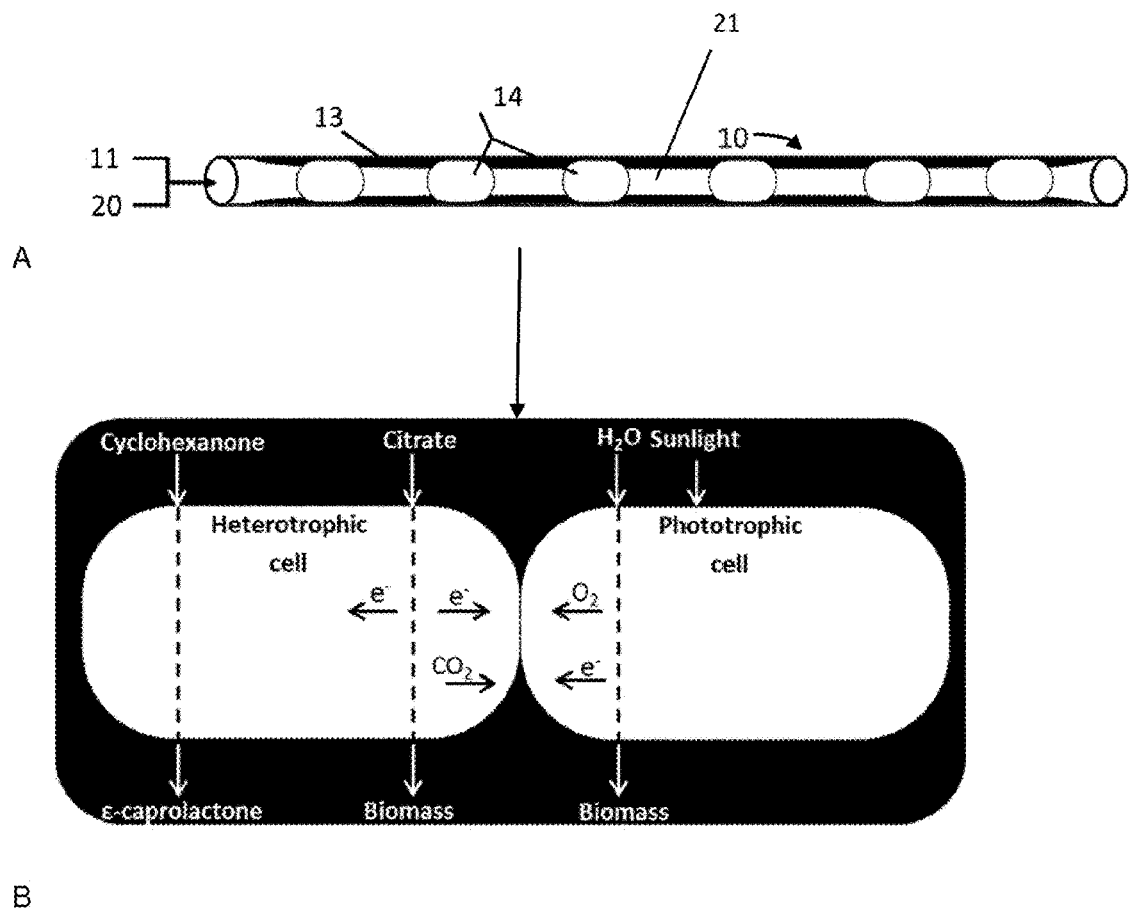
FIG. 3:
(A) Scheme of biofilm-based tubular capillary reactor.
(B) Schematic representation of proto-cooperation and cyclohexanone conversion to ε-caprolactone reaction within mixed-species biofilm containing *Synechocystis* sp. PCC 6803_alkBGT and *Pseudomonas* sp. VLB120_CHXON.
(C) Demonstrating application of the concept looking at continuous cyclohexanone conversion to s-caprolactone at the capillary outlet.
Figure 3:
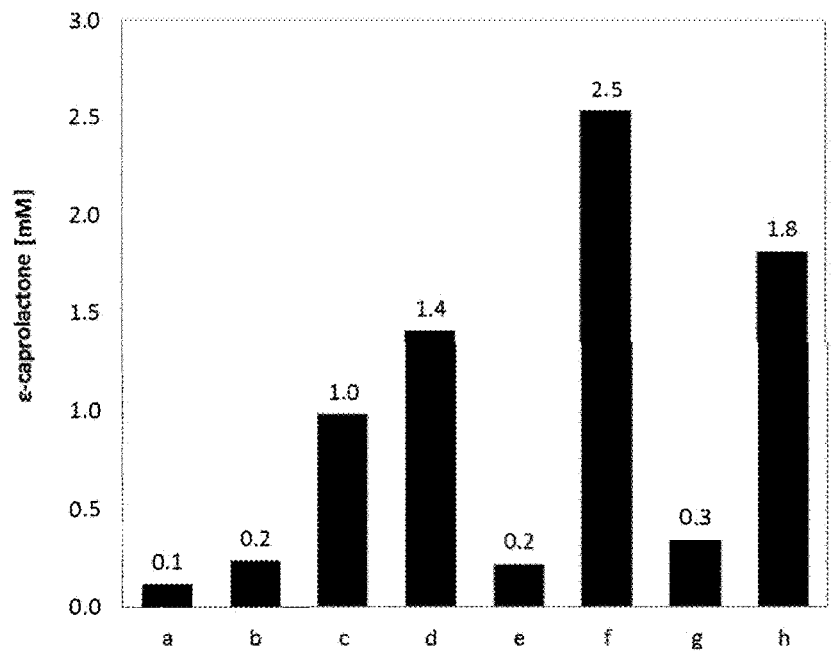

SEQ ID NO: 1 Primer PAH091 used in plasmid construction during cloning;
SEQ ID NO: 2 Primer PAH092 used in plasmid construction during cloning;
SEQ ID NO: 3 Primer PAH093 used in plasmid construction during cloning;
SEQ ID NO: 4 Primer PAH094 used in plasmid construction during cloning;
SEQ ID NO: 5 Primer PAH077 used in plasmid construction during cloning;
SEQ ID NO: 6 Primer PAH078 used in plasmid construction during cloning.

EXAMPLES

1. Methods

Chemicals

All chemicals used in this invention were purchased in the highest purity available from Carl-Roth GmbH (Karlsruhe, Germany), Merck (Darmstadt, Germany) or Sigma-Aldrich (Steinheim, Germany) and applied without any further purification.

Bacterial Strains and Plasmids

All strains and plasmids used in this method

| # | | Description | Ref |
|---|---|---|---|
| | Strains | | |
| 1 | Pseudomonas sp. VLB120 | Wild-type Pseudomonas; styrene prototroph | [1] |
| 2 | Ps_Km | Strain #1 harboring pRSF_Ptrc1O: Term (plasmid #10) | This invention |
| 3 | Ps_CYP | strain #1 harboring pCom10_CYP (plasmid #11) | This invention |
| 4 | Ps_BVMO | strain #1 harboring pRSF_Ptrc1O: BVMO (plasmid #15) | This invention |
| 5 | Synechocystis sp. PCC 6803 | Geographical origin: California, USA; Received from Pasteur Culture Collection of Cyanobacteria (PCC, Paris, France) | [2] |
| 6 | Syn6803_Km | Strain #5 harboring pRSF_Ptrc1O: Term (plasmid #10) | This invention |
| 7 | Syn_CYP | strain #5 harboring pRSF_Ptrc1O: CYP (plasmid #12) | This invention |
| 8 | Syn_BGT | Strain #5 harboring pRSF_Ptrc1O: BGT | [6] |
| 9 | E. coli DH5α | Cloning strain; genomic markers: F⁻ φ80IacZΔM15 Δ(lacZYA-argF) U169 recA1 endA1 hsdR17 (rK⁻, mK⁺) phoA supE44 λB⁻ thi⁻¹ gyrA96 relA1 | Invitrogen |
| | Plasmids | | |
| 10 | pRSF _ Ptrc1O: Term | pPMQAK1 based, RSF, $P_{mpB}$: lacI, $P_{trc1O}$: Term, empty cloning vector | [6] |
| 11 | pCom10_CYP | pCom10 derivative, with genes encoding for CypP450 monooxygenase (CHX), ferredoxin reductase (FdR), ferredoxin (Fd), from Acidovorax CHX100 | [3] |
| 12 | pRSF_Ptrc1O: CYP | pPMQAK1 derivative, containing the $P_{trc1O}$ as well as lacI promoter controlling the expression of CYP (Cytochrome P450 enzyme), ferredoxin (Fd) and ferredoxin reductase (FdR), from Acivodorax CHX100 | This invention |
| 13 | pCom10_capro | pCom10 derivative, with genes encoding for CypP450 monooxygenase (CHX), ferredoxin reductase (FdR), ferredoxin (Fd), cyclohexanone monooxygenase (CHXON) and cyclohexanol dehydrogenase (CDH) from Acidovorax CHX100 | [4] |
| 14 | pSB1AC3_Ptrc1O: GFPm ut3B | pMB1, biobrick #BBa_B0015 terminator sequence | [5] |
| 15 | pRSF_Ptrc1O: BVMO (=pAH49) | BVMO originating from Acidovorax sp. CHX100 under control of $P_{trc1O}$ promoter, with optimized ribosomal binding site RBS* in front of BVMO with C-terminal Strep-tag II | This invention |
| 16 | pRSF_Ptrc1O: BGT (=pAH042) | AlkBGT (alkane monooxygenase AlkB, rubredoxin AlkG and rubredoxin reductase AlkT) originating from Pseudomonas putida GPo1 under control of $P_{trc1O}$ promoter, with optimized ribosomal binding site RBS* in front of each gene with C-terminal Strep-tag II | [6] |

Construction of Plasmids

Plasmid construction was based on standard cloning procedures. E. coli DH5α was used for cloning purposes. Overnight cultures were inoculated from cryo-stock and grown in LB medium at 30° C. and 180 rpm (2.5 cm amplitude).[4] Primers used in this work are listed in the table below and were obtained from Eurofins Genomics (Ebersberg, Germany). The cloning strategy for constructing the plasmid pRSF_Ptrc1O:CYP and pRSF_Ptrc1O:BVMO is described below. Transformation of Synechocystis sp. PCC 6803 with the respective plasmids was performed by electroporation as described in Hoschek et al. 2017.[6]

| SEQ ID NO. | Primer# | Function | Primer used during cloning; binding region, overlap to vector, scar, RBS\*, *STOP*, StrepTagII Sequence |
|---|---|---|---|
| 1 | PAH091 | BVMO fwd | TGAGCGGATAACAATTTCACACATACTAGAGTAGTGGAGGT-TACTA GATGAAAAAAACCCAACATCTGG |
| 2 | PAH092 | BVMO rev | TCGTTTTATTTGATGCCTGGCTGCA*CTAT-TTTTCGAACTGCGGGTG* GCTCCAAGCGCTCTGGAATACGAAACCCTCG |
| 3 | PAH093 | CYP fwd | TGAGCGGATAACAATTTCACACATACTAGAGTAGTGGAGGT-TACTA GATGACTCAGACTGCTGCGGC |
| 4 | PAH094 | CYP rev | CTTTCGTTTTATTTGATGCCTGGTATCAGTGCTGCCCTTGCG |
| 5 | PAH077 | Term fwd | GGGAGGTATTGGACCGCATTGAACTCTAGTA TATAAACGCAGAAAG GCCC |
| 6 | PAH078 | Term rev | ACGAGCCGGATGATTAATTGTCAATCTAGAG CCAGGCATCAAATAA AACG |

Figure 4:
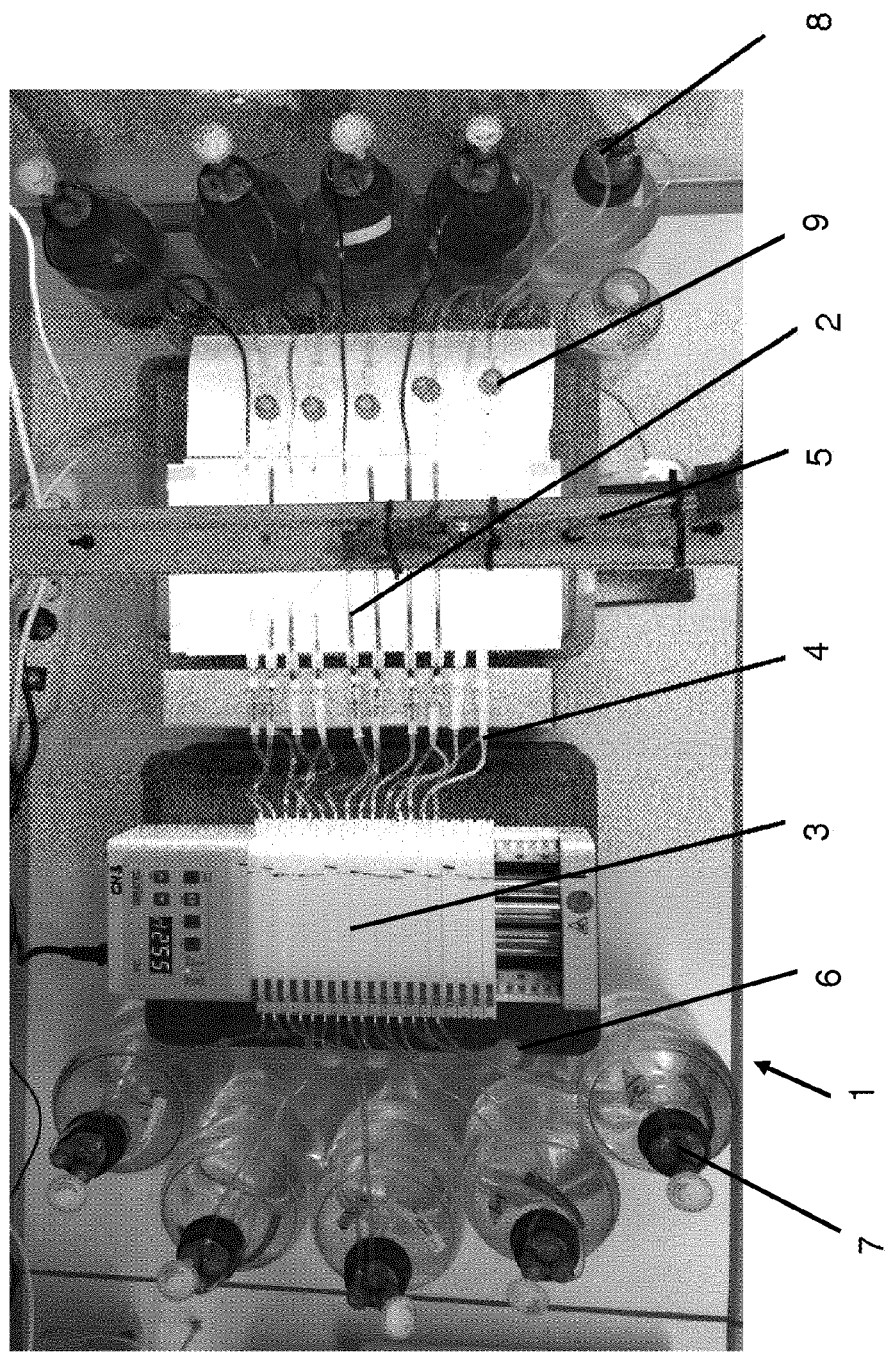
FIG. 4:
Technical setup of a segmented flow biofilm capillary reactor system.

Construction of pRSF_Ptrc1O:CYP
  Restriction: pRSF_Ptrc1O:Term with SpeI
  Amplification: CYP from pCom10_capro (PAH093+PAH094→2970 BP, TAn: 72° C., tElong: 60 sec)
  Gibson assembly: pRSF_Ptrc1O:Term (SpeI)+CYP→pRSF_Ptrc1O:CYP_pre (without Termcentral)
  Restriction: pRSF_Ptrc1O:CYP_pre with XbaI
  Amplification: Term from pSB1AC3_Ptrc1O:GFPmut3B (PAH077+PAH087→191 BP, TAn: 60° C., tElong: 5 sec)
  Gibson assembly: pRSF_Ptrc1O:CYP_pre (XbaI)+Term→pRSF_Ptrc1O:CYP
Construction of pRSF_Ptrc1O:BVMO Plasmid
  Restriction: pRSF_P$_{trc1O}$:Term with SpeI
  Amplification: BVMO from pCom10_capro (PAH091+PAH092→1689 BP, T$_{An}$: 72° C., t$_{Elong}$: 45 sec)
  Gibson assembly: pRSF_Ptrc1O: Term (SpeI)+BVMO→pRSF_P$_{trc1O}$:BVMO_pre (without Term$_{central}$)
  Restriction: pRSF_P$_{trc1O}$:BVMO_pre with XbaI
  Amplification: Term from pSB1AC3_Ptrc1O:GFPmut3B (PAH077+PAH087→191 BP, T$_{An}$: 60° C., t$_{Elong}$: 5 sec)
  Gibson assembly: pRSF_P$_{trc1O}$:BVMO_pre (XbaI)+Term→pRSF_P$_{trc1O}$:BVMO
Mixed Species Biofilm Cultivation in Capillary Reactors Harboring *Pseudomonas* VLB120 and *Synechocystis* PCC 6803
Pre-Cultivation of Syn6803 Km
  Pre-cultures of Syn6803_Km were grown in YBG11 medium: 1.49 g L$^{-1}$ NaNO$_3$, 0.074 g L$^{-1}$ MgSO$_4$·7H$_2$O, 0.305 g L$^{-1}$ K$_2$HPO$_4$, 10 mL L$^{-1}$ YBG11 trace elements (100×), 0.019 g L$^{-1}$ Na$_2$CO$_3$, 50 mM HEPES (pH 7.2); YBG11 trace elements (100×): 0.36 g L$^{-1}$ CaCl$_2$·2 H$_2$O, 0.28 g L$^{-1}$ boric acid, 0.11 g L$^{-1}$ MnCl$_2$·4H$_2$O, 0.02 g L$^{-1}$ ZnSO$_4$·7H$_2$O, 0.039 g L$^{-1}$ Na$_2$MoO$_4$·2H$_2$O, 0.007 g L$^{-1}$ CuSO$_4$·5H$_2$O, 0.003 g L$^{-1}$ Co(NO$_3$)$_2$·6H$_2$O, 0.1 g L$^{-1}$ FeCl$_3$·6H$_2$O, 0.6 g L$^{-1}$ Na$_2$EDTA·2H$_2$O, 4.2 g L$^{-1}$ NaHCO$_3$, supplemented with 50 μg/mL kanamycin as antibiotic selection marker.
  Pre-cultures were inoculated in 20 mL medium in a 100 mL baffled shake flask using 200 μL of cryo-stock and cultivation was carried out at 30° C., 50 μmol m$^{-2}$ s$^{-1}$ (LED), ambient CO$_2$ (0.04%), 150 rpm (2.5 cm amplitude), and 75% humidity in an orbital shaker (Multitron Pro shaker, Infors, Bottmingen, Switzerland) for 4 days. From this pre-culture, main-cultures were inoculated starting with an OD$_{750}$ of 0.08 and cultivation was continued for another 4 days.
Pre-Cultivation of Ps_Km
  Overnight cultures of Ps_Km were inoculated from a cryo-stock using 5 mL LB medium and grown at 30° C. and 200 rpm (2.5 cm amplitude) in an orbital shaker (Multitron Pro shaker, Infors, Bottmingen, Switzerland).[4] Pre-cultures were inoculated by adding 200 μL of this overnight-culture to 20 mL M9 medium (5 g L$^{-1}$ citrate, US* trace elements) and growth was continued for 24 h.[7] Main-cultures were grown for 8 h in 50 mL M9 medium (5 g L$^{-1}$ citrate, US* trace elements) in 250 mL baffled shake flasks starting with an OD$_{450}$ of 0.2.
Pre-Mixing of Bacterial Strains
  20 mL of each main culture (Syn_Km and Ps_Km) were centrifuged (5000 g, room temperature, 7 min), washed in 20 mL YBG11 (w/o citrate, 50 mM NaHCO$_3$) and resuspended in 40 mL YBG11 medium (supplemented with 50 mM NaHCO$_3$ to ensure sufficient carbon supply). Optical densities after resuspension were OD$_{750}$=2.3 and OD$_{450}$=2.3, respectively. 50 mL of Syn6803_Km were mixed with 50 mL of Ps_Km in a 500 mL baffled shake flask and cultivation was continued at 30° C., 50 μmol m$^{-2}$ s$^{-1}$ (LED), ambient CO$_2$ (0.04%), 150 rpm (2.5 cm amplitude), and 75% humidity in an orbital shaker (Multitron Pro shaker, Infors, Bottmingen, Switzerland) for 24 h. 10 mL of each single species control cultures were mixed with 10 mL of YBG11 medium (50 mM NaHCO$_3$) in a 100 mL baffled shake flask.
  For biofilm cultivation, a capillary reactor 1 system adapted from David et al. 2015 was applied (analogous to FIG. 4).[5] Serological pipettes functioned as capillaries 2 for biofilm growth (1 mL, trimmed to a tube volume of 1.2 mL by cutting the tip and the intake area; inner diameter of 3 mm, 16.6 cm length, Labsolute, Th. Geyer GmbH & Co. KG, Renningen, Germany). YBG11 medium (supplemented with 50 mM NaHCO$_3$) was supplied via Tygon tubing (LMT-55, 2.06 mm inner diameter, 0.88 mm wall thickness; Ismatec, Wertheim, Germany) using a peristaltic pump 3 (ISM939D; Ismatec, Wertheim, Germany). Air segments were supplied via Tygon tubing connected by a T-connector 4 to the reactor system. Fluorescence-light tubes were used as light source 5 (50 µmol m$^{-2}$ s$^{-1}$ measured at the center of tubular capillaries). Gas exchange at medium inlet 7, for air segments, and at medium outlet 8 was enabled through sterile filters 6 (0.2 µm). Cultivation was performed at room temperature (~26° C.). Headspace samples of the gas phase can be collected in a bubble trap 9.

Instead of the shown reactor design, reactor designs shown and described in WO 2012/152337 A1, particularly FIG. 1-5 of WO 2012/152337 A1, may be used.

Inoculation of Capillary Reactor System

The capillaries of the reactor system were inoculated with single and mixed species cultures, respectively, by purging with ca. 5 mL of each culture through the capillaries. Medium flow was started 15-18 h after inoculation at a rate of ~55 µL min$^{-1}$. If indicated, air segments were introduced 6-9 days after inoculation at a rate of ~55 µL min$^{-1}$, resulting in an increased overall flow rate of ~110 UL min$^{-1}$ in these tubes.

Light Spectra

Light spectra of applied light sources (LED in orbital shakers and fluorescence light-tubes in tubular capillary reactor setup) are given in Hoschek et al. 2017.[6]

Cultivation in the Capillary Reactor System without Organic Carbon Source

The mixed trophies biofilm consisting of Syn6803_Km and Ps_Km were supplied continuously with YBG11 medium supplemented with 50 mM NaCO$_3$ and 50 mg/L kanamycin as selection marker.

Cultivation Supplying Citrate as an Organic Carbon Source

Supplying citrate as organic carbon source during cultivation will facilitate Ps_Km growth. In such experiments, YBG11 medium was supplemented with 50 mM NaCO3, 50 mg/L kanamycin and 0.4 g/L citrate as organic carbon source.

Mixed Species Biofilm Cultivation in Capillary Reactors Harboring Ps_CYP and Syn_CYP Producing Cyclohexanol from Cyclohexane Pre-cultivation of *Synechocystis* sp. PCC 6803 with pRSF_Ptrc1O:CYP (Syn_CYP) and *Pseudomonas* sp. VLB120 with pCom10 CYP (Ps_CYP)

Cultures of *Synechocystis* sp. PCC 6803 with pRSF_Ptrc1O:CYP (Syn_CYP) and *Pseudomonas* sp. VLB120 with pCom10_CYP (Ps_CYP) were grown separately in YBG11 as described above.

Pre-Mixing of Ps_CYP and Syn_CYP and Inoculation of the Capillary Reactor

For the inoculation of the mixed species biofilm both species have been mixed as described above and subsequently the capillary reactor was inoculated with the mixed trophies culture.

Cyclohexanol Production Utilizing Mixed Trophies Biofilms of Ps_CYP and Syn_CYP in Capillary Reactors Gene expression of cyp in Syn_Cyp was induced after 21 days of cultivation by the addition of 2 mM IPTG supplied with the YBG11 medium. At day 22, cyclohexane feed was started. Cyclohexane, the substrate for the biotransformation, was delivered via air phase. The air flow was passed through a silicone tube, dipped into liquid cyclohexane allowing the cyclohexane to diffuse through the silicone tube into the air stream. The biotransformation was started with an equal ratio of medium (51 µL/min) and air flow and the product formed was measured at the outflow.

After 20 days of biotransformation, the light was turned off for 24 h and subsequently turned on again for 48 h. This process of tuning light off for 24 h was repeated once again.

Quantification of Cyclohexane and Cyclohexanol Using Gas Chromatography (GC)

For substrate (cyclohexane) and product (cyclohexanol) quantification in the liquid phase, reactor outflow was collected. 900 µL of sample were mixed with 900 µL of ice-cold ether, vortexed for 2 min, and centrifuged (17,000 g, 2 min, room temperature (rt)). The ether phase was removed and dried over anhydrous Na$_2$SO$_4$ and analyzed by gas chromatography.

In addition, cyclohexane was quantified in the gas phase. Headspace samples of the gas phase were collected in a bubble trap and manually applied to GC analysis using a Hamilton gas-tight syringe.

GC Method

Reactants were quantified using gas chromatography (GC Trace 1310, Thermo Fisher Scientific, Waltham, USA) equipped with a TG-5 MS capillary column (5% diphenyl/95% dimethyl polysiloxane, 30 m, I.D.: 0.25 mm, film thickness: 0.25 µm, ThermoFisher Scientific, Waltham, USA) and a flame ionization detector (FID) operating at 320° C., 350 mL min$^{-1}$ air flow, 30 mL min$^{-1}$ makeup gas flow and 35 mL min$^{-1}$ hydrogen gas flow. Nitrogen gas was applied as a carrier gas with a constant flow of 1.5 mL min$^{-1}$.

Liquid- and gas-sample injection volumes were 1 µL and 100 µL, respectively. The PTV inlet was programmed with a temperature gradient of 10° C. s$^{-1}$ from 90-300° C. A split ratio of 11 was applied. The temperature profile of the oven was set to: 1) 40° C. for 1 min, 2) 40-80° C. with 10° C. min$^{-1}$, 3) 80-250° C. with 100° C. min$^{-1}$, and 4) 250° C. for 2 min for both sample types.

Mixed Species Biofilm Cultivation in Capillary Reactors Harboring Ps_BVMO and Syn_BGT Producing Caprolactone from Cyclohexanone Pre-cultivation of *Synechocystis* sp. PCC 6803 with pRSF_Ptrc1O:BGT (Syn_BGT) and *Pseudomonas* sp. VLB120 with pRSF_Ptrc1O:BVMO (Ps_BVMO)

Cultures of *Synechocystis* sp. PCC 6803 with pRSF_Ptrc1O:BGT (Syn_BGT) and *Pseudomonas* sp. VLB120 with pRSF_Ptrc1O:BVMO (Ps_BVMO) were grown separately in YBG11 as described above.

Pre-Mixing of Ps_BVMO and Syn_BGT and Inoculation of the Capillary Reactor

For the inoculation of the mixed species biofilm both species have been mixed as described above and subsequently the capillary reactor was inoculated with the mixed trophies culture.

ε-Caprolactone Production Utilizing Mixed Trophies Biofilms of Syn_BGT and Ps_BVMO in Capillary Reactors After 15 days of cultivation gene expression of bvmo was induced using 2 mM of IPTG supplied with the YBG11 medium. After 24 hours of induction the substrate cyclohexanone was added to the YBG11 medium (5 mM) and was constantly supplied with the feed.

Quantification of Cyclohexanone and Caprolactone Using Gas Chromatography (GC)

After 12 minutes of sampling, 600 µL of the outflow from the capillary reactor were mixed with 600 µL of ice-cold diethyl ether (containing 0.2 mM decane as internal standard) and extraction of cyclohexanone and caprolactone in the ether phase was supported by vortexing and subsequent centrifugation (17000 g, 5 min, rt). The ether phase was dried over anhydrous Na$_2$SO$_4$ and subjected to gas chromatography (GC Trace 1310, Thermo Fisher Scientific, Waltham, USA) equipped with a TG-5 MS capillary column (5% diphenyl/95% dimethyl polysiloxane, 30 m, I.D.: 0.25 mm, film thickness: 0.25 µm, ThermoFisher Scientific, Waltham, USA) and a flame ionization detector (FID) operating at 320° C., 350 mL min$^{-1}$ air flow, 30 mL min$^{-1}$ makeup gas flow and 35 mL min$^{-1}$ hydrogen gas flow. Nitrogen gas was applied as carrier gas with a constant flow of 1.5 mL min$^{-1}$. The injection volume was set to 1 μL using a PTV injector, programmed with a temperature gradient of 10° C. s$^{-1}$ from 90-300° C. A split ratio of 11 was applied. The oven temperature profile was: 1) 40° C. for 3 min, 2) 40-170° C. with 15° C. min$^{-1}$, 3) 170-300° C. with 100° C. min$^{-1}$, and 4) 300° C. for 1 min.

REFERENCES (METHOD SECTION ONLY)

[1] M. G. Panke, S; Witholt, B; Schmid, A; Wubbolts, "Towards a biocatalyst for (S)-styrene oxide production: characterization of the styrene degradation pathway of *Pseudomonas* sp. strain VLB120," Appl Env Microbiol 1998; 64:2032-2043.

[2] R. Y. Stanier, R. Kunisawa, M. Mandel, and G. Cohen-Bazire, "Purification and properties of unicellular blue-green algae (Order Chroococcales)," Bacteriol Rev 1971; 35:171-205.

[3] R. Karande et al., "Continuous cyclohexane oxidation to cyclohexanol using a novel cytochrome P450 monooxygenase from Acidovorax sp. CHX100 in recombinant *P. taiwanensis* VLB120 biofilms," Biotechnol Bioeng 2016; 113:52-61.

[4] T. Sambrook, J and Russell, D W and Maniatis, Molecular cloning. 2001.

[5] A. David, C.; Bühler, K.; Schmid, "Stabilization of single species *Synechocystis* biofilms by cultivation under segmented flow," J Ind Microbiol Biotechnol 2015; 42: 1083-1089.

[6] A. Hoschek, A.; Bühler, B.; Schmid, "Overcoming the Gas-Liquid Mass Transfer of Oxygen by Coupling Photosynthetic Water Oxidation with Biocatalytic Oxyfunctionalization," Angew Chemie Int Ed 2017; 56:15146-15149.

[7] Emmerling, M., et al., Metabolic flux responses to pyruvate kinase knockout in *Escherichia coli*. *J Bacteriol* 2002; 184:152-164.

2. Results Part 1-Mixed Species Biofilm Cultivation in Capillary Reactors Harboring *Pseudomonas* sp. VLB120 and *Synechocystis* sp. PCC 6803

To validate the technique of co-cultivating mixed-trophies biofilms in a capillary reactor, the two model strains *Synechocystis* sp. PCC 6803 and *Pseudomonas* sp. VLB120 were applied carrying a kanamycin resistance cassette, resulting in Syn6803_Km and Ps_Km, respectively. Both strains were pre-grown separately in shake flasks and subsequently mixed in a ratio of 1:1 (based on optical density) before inoculation of the capillary reactor. Serological pipettes (1.2 mL tube volume, 16.6 cm length, 3 mm inner diameter) functioned as light-transmissive capillary reactors for biofilm growth. The system was kept idle for 15 h to allow cell attachment before a constant medium flow of 55 μL min$^{-1}$ through the capillaries was applied. The supplied YBG11 medium was supplemented with 50 mM NaHCO$_3$, providing sufficient inorganic carbon (CO$_2$) for Syn_Km growth. The principle of proto-cooperation was examined by measuring the O$_2$ concentration in the liquid and gas phase, as well as citrate consumption. Cultivation was conducted for five weeks until the cultivation system was actively terminated and characterized regarding photo-pigment formation (macroscopic), bio-volume of each species (cell number and cell volume), and total biofilm dry weight (Table 1).

Four experimental setups, with and without citrate as an organic carbon source, and in the presence or absence of air segments were operated (FIG. 1). Also, single species cultures served as control experiments (FIG. 1). In FIG. 1C following experiments are shown:

Mixed species biofilm (Syn_Km and Ps_Km)
i) without citrate/without air segments
ii) without citrate/with air segments
iii) 0.4 g/L citrate/without air segments
iv) 0.4 g/L citrate/with air segments
Single species biofilm as controls
v) Syn_Km without citrate/without air segments
vi) Syn_Km without citrate/with air segments
vii) Syn_Km 0.4 g/L citrate/without air segments
viii) Syn_Km 0.4 g/L citrate/with air segments
ix) Ps_Km 0.4 g/L citrate/without air segments
x) Ps_Km 0.4 g/L citrate/with air segments Cultivation without Organic Carbon Source Cultivating the biofilm only with inorganic carbon (NaHCO$_3$), supports mainly the growth of the photoautotrophic strain. After five weeks of cultivation without air segments, the capillary was unevenly coated with cyanobacterial biofilm. Most of the biomass was located in the first part of the capillary (FIG. 1 Ci). Strikingly, the O$_2$ content measured in the aqueous medium has been 3.5 fold above the saturation limit at ambient conditions (Table 1). Most likely these extreme O$_2$ concentrations led to oxidative stress for Syn6803_km, resulting in visible photo-pigment reduction (yellowish/light green outer appearance of the strain) towards the end of the capillary and hampered growth. Due to the missing organic carbon source, also Ps_km could not well develop, as was expected under these cultivation conditions. The final total biofilm dry weight was rather low (~6 $g_{BDW}$ L$^{-1}$) and mainly consisted of cyanobacterial cells.

The application of air segments clearly promoted biofilm formation resulting in a lush green biofilm throughout the length of the capillary (FIG. 1 Cii). Excess O$_2$ was extracted from the liquid medium to the gas phase, increasing the O$_2$ concentration from 21 to ~24% and thus relieving the oxidative stress on the cyanobacteria located in the aqueous phase. In comparison to capillaries containing Syn_Km only (FIG. 1 Cv and Cvi), the final biofilm dry weight was improved from 14 to 32 $g_{BDW}$ L$^{-1}$ mainly consisting of cyanobacterial cells. In addition to the critical role of O$_2$, the presence of the heterotrophic cells supported cyanobacterial biofilm formation. *Pseudomonas* probably survived on EPS or cell debris, as no other organic carbon source was present. Despite the very low ratios of Ps_Km, the excellent biofilm forming capabilities of *Pseudomonas* sp. VLB120 may have fostered adherence of the cyanobacterial strain.

Cultivation Supplying Citrate as an Organic Carbon Source

Supplying citrate as organic carbon source during cultivation will facilitate Ps_Km growth, while Syn_Km cells deliver O$_2$ from photosynthetic water oxidation. After five weeks of cultivation in YBG11 medium supplemented with citrate, the capillaries were thoroughly coated with rich green biofilm (FIG. 1 Ciii and Civ). Without air segments, citrate respiration of Ps_Km decreased the O$_2$ concentration in the aqueous phase down to anoxic conditions. Due to the in situ supply of O$_2$, the presence of cyanobacterial cells enhanced the biovolume of Ps_Km 20-fold and the citrate uptake 9-fold in comparison to single species Ps_Km. From the perspective of Syn_Km, the reduction of oxidative stress due to Ps_Km respiration had a positive impact on cyanobacterial growth. This is reflected by a four times increased Syn_Km biovolume in comparison to single species Syn_Km (Cvii). The final total biomass accounted for 48 $g_{BDW}$ $L^{-1}$, consisting of both species in a ratio of 6:1 Syn_Km:Ps_Km.

Upon the addition of air segments, the citrate uptake rate increased and no residual citrate could be detected in the outflow of the reactor (Civ). Furthermore, $O_2$ was stripped to the gas phase and increased oxygen partial pressure in the air segments by ~3% in comparison to the Ps_Km single species (Cx). It seems as if the absence of air segments in this particular setting is beneficial for the development of *Pseudomonas* sp. VLB120 (Ciii). Introducing air segments leads to high fluidic and interfacial stresses in the capillary, which in turn might require more energy for *Pseudomonas* maintenance (Ciii).

This approach is based on proto-cooperation, which is the beneficial, but not essential, interaction of organisms resulting in e.g., enhanced growth. It is a simple way to operate high cell density biofilm capillary reactors for various biocatalytic applications in a continuous mode. The method allows high cell density cultivation of photoautotrophs, which is currently a key-bottleneck in photo-biotechnology. Furthermore, coupling photosynthetic $O_2$ generation with bacterial respiration in a biofilm capillary reactor extends the process boundary of $O_2$-limited bioprocesses.

This concept now awaits the implementation of biocatalytically active strains and scale-up for the eco-efficient production of chemicals. Next to biocatalytic applications, mixed-trophies biofilms could be a valuable tool for other research fields, such as bioremediation or ecotoxicology.

TABLE 1

Quantitative data obtained from single and mixed species biofilm cultivation in a tubular capillary reactor. Syn. = Syn6803_Km, Ps. = Ps_Km, Mixed sp. = Co-culture of Syn6803_Km and Ps_Km, −Citrate = without organic carbon source, +Citrate = with 0.39 g $L^{-1}$ citrate as carbon source, −Air = without air segments, +air = with air segments.

| Experimental setup | | $O_2$ in gas phase/ % | $O_2$ in aq. phase [1]/ μM | Citrate consumption/ g $L^{-1}$ | Biovolume [2, 3, 4]/ $mm^3$ $mL^{-1}$ | | Biofilm dry weight [3]/ g $L^{-1}$ |
|---|---|---|---|---|---|---|---|
| | | | | | Ps. | Syn. | |
| Mixed sp. | −Air | — | 922 | — | 0.1 | 8.4 | 6 |
| −Citrate | +Air | 24.1 | — | — | 0.3 | 45 | 32 |
| Mixed sp. | −Air | — | 0 | 0.27 | 6.4 | 36 | 48 |
| +Citrate | +Air | 16.3 | — | 0.39 | 1.5 | 17 | 19 |
| Single Syn. | −Air | — | 745 | — | — | 1.4 | 2 |
| −Citrate | +Air | 23.9 | — | — | — | 19 | 14 |
| Single Syn. | −Air | — | 993 | 0 | — | 1.4 | 1 |
| +Citrate | +Air | 23.6 | — | 0 | — | 2.7 | 3 |
| Single Ps. | −Air | — | — | 0.03 | 0.3 | — | 1 |
| +Citrate | +Air | 13.4 | — | 0.38 | 1.6 | — | 5 |

[1] Solubility of $O_2$ (at 26° C., salinity of 3.5 g $kg^{-1}$): ~250 μM (21% $O_2$) and ~1190 μM (100% $O_2$)
[2] based on cell number and cell volume measured by Coulter Counter
[3] based on 1.2 mL tube volume
[4] a fraction of 0.2 $mm^3$ $mL^{-1}$ measured by Coulter Counter was attributed to elongated Ps_Km cells after microscopic analysis Discussion/Conclusion of Results Part 1

The heterotrophic biocatalyst *Pseudomonas* sp. VLB120 was already investigated in several studies for the continuous production of chemicals in biofilm capillary reactors (Gross, R. et al., *Biotechnol. Bioeng.* 105, 705-717 (2010); Karande, R. et al., *Org. Process Res. Dev.* 20, 361-370 (2016)). In contrast, phototrophic organisms show biofilm formation mainly in wastewater treatment plants (Barros, A. C. et al., *J. Appl. Phycol.*, 1-13 (2018)), whereas the cyanobacterial model strain *Synechocystis* sp. PCC 6803 was recently applied for studying the biofilm formation in capillaries (David, C. et al., *J. Ind. Microbiol. Biotechnol.* 42, 1083-1089 (2015)).

In this invention, co-cultivation of the two species significantly enhanced biofilm formation in comparison to the cultivation as single species.
  i) In a mixed trophies biofilm it was possible to cultivate the photoautotrophic *Synechocystis* sp. PCC 6803 over a time-period of five weeks to a high cell density of max. 48 $g_{BDW}$ $L^{-1}$.
  ii) Growth of the heterotroph aerobe *Pseudomonas* sp. VLB120 was 20 times enhanced solely due to the in situ supply of $O_2$ originating from the photosynthetic water oxidation of the co-cultured cyanobacterium.

3. Results Part 2-Mixed Species Biofilm Cultivation in Capillary Reactors Harboring Ps_CYP and Syn_CYP Producing Cyclohexanol from Cyclohexane A scheme of biofilm-based tubular capillary reactor is shown in FIG. 2A. CHX in FIG. 2A means cyclohexane, which was delivered via the air segments in gaseous form.

FIG. 2B is a schematic representation of proto-cooperation and reaction within mixed-species biofilm containing *Synechocystis* sp. PCC 6803_CHX and *Pseudomonas* sp. VLB120_CHX. The catalytic function of cyclohexane oxidation was introduced by genetic modification into both *Synechocystis* and *Pseudomonas* as described above.

FIG. 2C shows that a stable mixed species biofilm was obtained that shows catalytic activity for the conversion of cyclohexane to cyclohexanol over long time periods.

Moreover, FIG. 2C shows that the production of cyclohexanol from cyclohexane is light dependent.

4. Results Part 3-Mixed Species Biofilm Cultivation in Capillary Reactors Harboring Ps_BVMO and Syn_BGT Producing Caprolactone from Cyclohexanone A scheme of the biofilm-based capillary reactor is shown in FIG. 3A. The substrate in FIG. 3A means cyclohexanone, which was delivered via the aqueous segments through the media.

FIG. 3B is a schematic representation of proto-cooperation and reaction within mixed species biofilm containing Syn_BGT and Ps_BVMO. The catalytic function of cyclohexanone oxidation was introduced by genetic modification into the *Pseudomonas* species as described above.

In FIG. 3C results of following experiments are shown:
a mixed species, without citrate/without air segments
b mixed species, without citrate/with air segments
c mixed species, 0.1 g/L citrate/without air segments
d mixed species, 0.1 g/L citrate/with air segments
e mixed species, 0.5 g/L citrate/without air segments
f mixed species, 0.5 g/L citrate/with air segments
g mixed species, 5 g/L citrate/without air segments
h mixed species, 5 g/L citrate/with air segments FIG. 3C shows catalytic activity in conversion of cyclohexanone to s-caprolactone. FIG. 3C also shows that heterotrophic cells extract excess of $O_2$ by respiration and catalysis.

LIST OF REFERENCE SYMBOLS 1 reactor (system)
2 capillary member
3 pump
4 T-connector
5 light source
6 filter
7 medium inlet
8 medium outlet
9 bubble trap
10 capillary member; tubular capillary reactor; carrier
11 air
12 medium
13 biofilm
14 segments of a gaseous phase: air segments
15 components of biofilm: extracellular polymeric substances
16 photoautotrophic microorganisms: cyanobacterial cells
17 chemoheterotrophic microorganisms: *pseudomonas* cells
18 light
19 air+substrate cyclohexane (CHX)
20 aqueous medium+substrate cyclohexanone
21 segments of liquid phase

---

The invention claimed is:

1. A biofilm composition having a cell density of 30 grams of cell dry weight per liter or more, comprising: photoautotrophic *Synechocystis* which produce oxygen by photosynthetic water oxidation; chemoheterotrophic *Pseudomonas taiwanensis* which respire oxygen; and components which are secreted by the *Synechocystis* and/or the *Pseudomonas taiwanensis*, wherein the *Synechocystis* and/or the *Pseudomonas taiwanensis* are genetically modified to express cytochrome P450 for the conversion of cyclohexane to cyclohexanol, or genetically modified to express cyclohexanone monooxygenase for the conversion of cyclohexanone to ε-caprolactone.

2. The biofilm composition of claim 1, wherein the biofilm is adhered to a surface of a carrier.

3. The biofilm composition of claim 2, wherein the carrier is a flat carrier, a tube or a capillary.

4. The biofilm composition of claim 1, wherein the thickness of the biofilm is from about 10 µm to about 500 µm.

5. A reactor comprising the biofilm composition of claim 1, wherein the biofilm extends along a surface of the reactor.

6. The reactor of claim 5, wherein the reactor is a capillary reactor comprising at least one capillary member made from a translucent material, and wherein the biofilm adheres to an inner surface of an at least one capillary member.

7. A method for producing the biofilm composition according to claim 1, the method comprising cultivating a mixture of the *Synechocystis* and the *Pseudomonas taiwanensis* on a surface, wherein the *Synechocystis* and/or the *Pseudomonas taiwanensis* are genetically modified to express cytochrome P450 for the conversion of cyclohexane to cyclohexanol, or genetically modified to express cyclohexanone monooxygenase for the conversion of cyclohexanone to ε-caprolactone.

8. The method of claim 7, further comprising exposing the mixture to light.

9. The method of claim 7, further comprising adding a substrate which is naturally metabolized by the *Pseudomonas taiwanensis*.

10. The method of claim 7, wherein the surface is of a capillary member in a capillary reactor, the method further comprising passing a gaseous phase and a liquid phase through the capillary member in alternation.

11. The biofilm composition of claim 1, wherein the substrate is cyclohexane and the product is cyclohexanol.

12. The biofilm composition of claim 2, wherein the carrier is made from glass, ceramic, plastic, metal, or a combination thereof.

13. The biofilm composition of claim 2, wherein the carrier is made from a translucent material.

14. The biofilm composition of claim 1, wherein the substrate is cyclohexanone and the product is ε-caprolactone.

* * * * *